(12) United States Patent
Aschmann et al.

(10) Patent No.: US 8,870,890 B2
(45) Date of Patent: Oct. 28, 2014

(54) PRONGED HOLDER FOR TREATING SPINAL STENOSIS

(75) Inventors: Felix Aschmann, Basel (CH); Peter Senn, Waldenburg (CH); Michael Mayer, Graefelfing (DE); Paul Pavlov, Nijmegen (NL)

(73) Assignee: DePuy Synthes Products, LLC, Raynham, MA (US)

( * ) Notice: Subject to any disclaimer, the term of this patent is extended or adjusted under 35 U.S.C. 154(b) by 1226 days.

(21) Appl. No.: 11/997,880

(22) PCT Filed: Aug. 3, 2006

(86) PCT No.: PCT/US2006/030614
§ 371 (c)(1),
(2), (4) Date: Jul. 1, 2008

(87) PCT Pub. No.: WO2007/019391
PCT Pub. Date: Feb. 15, 2007

(65) Prior Publication Data
US 2009/0012528 A1    Jan. 8, 2009

Related U.S. Application Data

(63) Continuation-in-part of application No. 11/198,393, filed on Aug. 5, 2005, now Pat. No. 7,753,938.

(60) Provisional application No. 60/795,883, filed on Apr. 27, 2006.

(51) Int. Cl.
*A61B 17/88* (2006.01)
*A61B 17/70* (2006.01)
*A61B 17/84* (2006.01)
*A61B 19/00* (2006.01)

(52) U.S. Cl.
CPC ........... *A61B 17/7065* (2013.01); *A61B 17/848* (2013.01); *A61B 19/54* (2013.01); *A61B 17/8897* (2013.01)
USPC ........................................................ 606/99

(58) Field of Classification Search
USPC ............................ 606/99, 100, 104, 205–211
See application file for complete search history.

(56) References Cited

U.S. PATENT DOCUMENTS

| 2,677,369 A | 5/1954 | Knowles |
| 3,648,691 A | 3/1972 | Lumb et al. |

(Continued)

FOREIGN PATENT DOCUMENTS

| FR | 2625097 | 6/1989 |
| FR | 2700941 | 8/1994 |

(Continued)

OTHER PUBLICATIONS

Benzel, et al., "Posterior cervical interspinous compression wiring and fusion for mid to low cervical spinal injuries," J. Neurosurg., 1989, pp. 893-899, vol. 70.

(Continued)

*Primary Examiner* — Mary Hoffman
(74) *Attorney, Agent, or Firm* — Meunier Carlin & Curfman, LLC

(57) ABSTRACT

A device for holding a surgical instrument having a body, an instrument engagement device and a knob. The body has a proximal end, a distal end and a passageway positioned through the body. The instrument engagement device is positioned in the passageway and has at least two prongs moveable relative to each other to hold the surgical instrument therebetween. The knob is preferably positioned on the proximal end of the body and operatively associated with the at least two prongs so that movement of the knob causes movement of the prongs. The prongs may further include at least one ridge for engaging at least one slot on the surgical instrument. The knob may further comprise a cap at its proximal end positioned and designed for impact, for example, by a hammer, to facilitate movement of the surgical instrument into the patient. The knob may also include a locking mechanism to fix the position of the prongs.

14 Claims, 19 Drawing Sheets

(56) References Cited

U.S. PATENT DOCUMENTS

| | | | |
|---|---|---|---|
| 4,174,715 A * | 11/1979 | Hasson | 606/206 |
| 4,393,872 A * | 7/1983 | Reznik et al. | 604/264 |
| 5,059,193 A | 10/1991 | Kuslich | 606/61 |
| 5,098,433 A | 3/1992 | Freedland | |
| 5,152,792 A | 10/1992 | Watkins et al. | |
| 5,306,309 A | 4/1994 | Wagner et al. | |
| 5,357,983 A | 10/1994 | Mathews | |
| 5,496,318 A | 3/1996 | Howland et al. | 606/61 |
| 5,575,790 A | 11/1996 | Chen et al. | |
| 5,653,763 A | 8/1997 | Errico et al. | |
| 5,702,391 A | 12/1997 | Lin | |
| 5,772,661 A | 6/1998 | Michelson | |
| 5,797,959 A * | 8/1998 | Castro et al. | 606/207 |
| 5,800,547 A | 9/1998 | Schafer et al. | |
| 6,102,950 A | 8/2000 | Vaccaro | |
| 6,235,030 B1 | 5/2001 | Zucherman et al. | 606/61 |
| 6,332,882 B1 | 12/2001 | Zucherman et al. | 606/61 |
| 6,332,883 B1 | 12/2001 | Zucherman et al. | 606/61 |
| 6,419,676 B1 | 7/2002 | Zucherman et al. | 606/61 |
| 6,451,019 B1 | 9/2002 | Zucherman et al. | 606/61 |
| 6,500,177 B1 | 12/2002 | Martinelli et al. | 606/57 |
| 6,652,527 B2 | 11/2003 | Zucherman et al. | 606/61 |
| 6,695,842 B2 | 2/2004 | Zucherman et al. | 606/61 |
| 6,699,246 B2 | 3/2004 | Zucherman et al. | 606/61 |
| 6,699,247 B2 | 3/2004 | Zucherman et al. | 606/61 |
| 6,733,534 B2 | 5/2004 | Sherman | 623/17.16 |
| 6,761,720 B1 | 7/2004 | Senegas | |
| 6,860,894 B1 * | 3/2005 | Pittman | 606/205 |
| 6,946,000 B2 | 9/2005 | Senegas et al. | |
| 7,029,473 B2 | 4/2006 | Zucherman et al. | 606/61 |
| 7,097,648 B1 | 8/2006 | Globerman et al. | |
| 7,201,751 B2 | 4/2007 | Zucherman et al. | 606/61 |
| 7,238,204 B2 | 7/2007 | Le Couedic et al. | |
| 2003/0149438 A1 * | 8/2003 | Nichols et al. | 606/99 |
| 2004/0010312 A1 | 1/2004 | Enayati | |
| 2004/0220568 A1 | 11/2004 | Zucherman et al. | 606/61 |
| 2005/0049590 A1 | 3/2005 | Alleyne et al. | |
| 2005/0055031 A1 | 3/2005 | Lim | |
| 2005/0143738 A1 | 6/2005 | Zucherman et al. | 606/61 |
| 2005/0203512 A1 | 9/2005 | Hawkins et al. | 606/61 |
| 2005/0203624 A1 | 9/2005 | Serhan et al. | 623/17.11 |
| 2005/0209603 A1 | 9/2005 | Zucherman et al. | 606/90 |
| 2005/0228383 A1 | 10/2005 | Zucherman et al. | 606/61 |
| 2005/0261768 A1 | 11/2005 | Trieu | 623/17.11 |
| 2006/0084988 A1 | 4/2006 | Kim | 606/61 |
| 2006/0085069 A1 | 4/2006 | Kim | 623/17.11 |
| 2006/0085070 A1 | 4/2006 | Kim | 623/17.11 |
| 2006/0095136 A1 | 5/2006 | McLuen | |
| 2006/0184247 A1 | 8/2006 | Edidin et al. | 623/17.11 |
| 2006/0184248 A1 | 8/2006 | Edidin et al. | 623/17.11 |
| 2006/0241601 A1 | 10/2006 | Trautwein et al. | 606/61 |
| 2006/0264938 A1 | 11/2006 | Zucherman et al. | 606/61 |
| 2006/0271049 A1 | 11/2006 | Zucherman et al. | 606/61 |
| 2007/0010813 A1 | 1/2007 | Zucherman et al. | 606/61 |
| 2007/0032790 A1 | 2/2007 | Aschmann | 606/61 |
| 2007/0043361 A1 | 2/2007 | Malandain et al. | 606/61 |
| 2007/0043362 A1 | 2/2007 | Malandain et al. | 606/61 |
| 2007/0043363 A1 | 2/2007 | Malandain et al. | 606/61 |
| 2007/0049934 A1 | 3/2007 | Edidin et al. | 606/61 |
| 2007/0049935 A1 | 3/2007 | Edidin et al. | 606/61 |
| 2007/0055237 A1 | 3/2007 | Edidin et al. | 606/61 |
| 2007/0093830 A1 | 4/2007 | Zucherman et al. | 606/61 |
| 2007/0173832 A1 | 7/2007 | Tebbe et al. | 606/61 |
| 2007/0203493 A1 | 8/2007 | Zucherman et al. | 606/61 |
| 2007/0203497 A1 | 8/2007 | Zucherman et al. | 606/61 |
| 2007/0203501 A1 | 8/2007 | Zucherman et al. | 606/61 |
| 2007/0208347 A1 | 9/2007 | Zucherman et al. | 606/61 |
| 2007/0219552 A1 | 9/2007 | Zucherman et al. | 606/61 |
| 2007/0225706 A1 | 9/2007 | Clark et al. | 606/61 |

FOREIGN PATENT DOCUMENTS

| | | |
|---|---|---|
| FR | 2717675 | 9/1995 |
| JP | 9075381 | 3/1997 |
| WO | WO 94/26192 | 11/1994 |
| WO | WO 2005/009300 A1 | 2/2005 |
| WO | WO 2006/045094 A2 | 4/2006 |
| WO | WO 2006/064356 A1 | 6/2006 |
| WO | WO 2006/102269 A2 | 9/2006 |

OTHER PUBLICATIONS

Caserta, et al., "Elastic stabilization alone or combined with rigid fusion in spinal surgery: a biomechanical study and clinical experience based on 82 cases," Eur. Spine J., Oct. 2002, pp. S192-S197, vol. 11, Suppl. 2.

Christie, et al., "Dynamic Interspinous Process Technology," SPINE, 2005, pp. S73-S78, vol. 30, No. 16S.

Cousin Biotech, "Analysis of Clinical Experience with a Posterior Shock Absorbing Implant," date unknown, pp. 2-9.

Cousin Biotech, Dispositif Intervertebral Amortissant, Jun. 1998, pp. 1-4.

Cousin Biotech, Technique Operatoire De La Prothese DIAM, date unknown, Annexe 1, pp. 1-8.

Dickman, et al., "The interspinous method of posterior atlantoaxial arthrodesis," J. Neurosurg., 1991, pp. 190-198, vol. 74.

Dispositivo Intervertebrale Ammortizzante "DIAM", date unknown, p. 1.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara, et al., "Intraoperative Measurement of Lumbar Spinal Instability," SPINE, 1992, pp. S44-S50, vol. 17, No. 3S.

Fassio, et al., "Treatment of Degenerative Lumbar Spinal Instability L4-L5 by Interspinous Ligamentoplasty," Rachis, Dec. 1991, pp. 465-473, vol. 3, No. 6.

Fassio, "Mise Au Point Sur La Ligamentoplastie Inter-Epineuse Lombaire Dans Les Instabilites," Maîtrise Orthopédique, Jul. 1993, pp. 18, No. 25.

Garner, et al., "Development and preclinical testing of a new tension-band device for the spine: the Loop System," Eur. Spine J., Aug. 7, 2002, pp. S186-S191, vol. 11, Suppl. 2.

Guang, et al., "Interspinous Process Segmental Instrumentation with Bone-Button-Wire for Correction of Scoliosis," Chinese Medical J., 1990, pp. 721-725, vol. 103.

Guizzardi, et al., "The use of DIAM (Interspinous Stress-Breaker Device) in the Prevention of Chronic Low Back Pain in Young Patients Operated on for Large Dimension Lumbar Disc Herniation," 12th Eur. Congress of Neurosurgery (EANS), Sep. 7-12, 2003, pp. 835-839, Lisbon, Portugal.

Hambly, et al., "Tension Band Wiring-Bone Grafting for Spondylolysis and Spondylolisthesis," SPINE, 1989, pp. 455-460, vol. 14, No. 4.

Kiwerski, "Rehabiliitation of patients with thoracic spine injury treated by spring alloplasty," Int. J. Rehab. Research, 1983, pp. 469-474, vol. 6, No. 4.

Laudet, et al., "Comportement Bio-Mécanique D'Un Ressort Inter-Apophysaire Vertébral Postérieur Analyse Expérimentale Du Comportement Discal En Compression Et En Flexion/Extenstion," Rachis, 1993, vol. 5, No. 2.

Lindsey, et al., "The Effects of an Interspinous Implant on the Kinematics of the Instrumented and Adjacent Levels in the Lumbar Spine," SPINE, 2003, pp. 2192-2197, vol. 28, No. 19.

Mah, et al., "Threaded K-Wire Spinous Process Fixation of the Axis for Modified Gallie Fusion in Children and Adolescents," Journal of Pediatric Orthopaedics, 1989, pp. 675-679, vol. 9, No. 6.

Mariottini, et al., "Preliminary results of a soft novel lumbar intervertebral prothesis (DIAM) in the degenerative spinal pathology," Acta Neurochirurgica, Advanced Peripheral Nerve Surgery and Minimal Invasive Spinal Surgery, Alexandre, et al., eds., 2005, pp. 129-131, Suppl. 92.

McDonnell, et al., "Posterior Atlantoaxial Fusion: Indications and Techniques," Techniques in Spinal Fusion and Stabilization, Hitchon et al., eds., 1995, pp. 92-106, Ch. 9, Thieme, New York.

(56) References Cited

OTHER PUBLICATIONS

Muller, "Restauration dynamique de la stabilite rachidienne," Tire de la Sulzer Technical Review, Jan. 1999, Sulzer Management Ltd, Winterthur, Switzerland.

Minns, et al., "Preliminary Design and Experimental Studies of a Novel Soft Implant for Correcting Sagittal Plane Instability in the Lumbar Spine," SPINE, 1997, pp. 1819-1825, vol. 22, No. 16.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini, et al., "Analisi Di Un'Esperienza Clinica Con Un Impianto Posteriore Ammortizzante," S.O.T.I.M.I. Societa di Ortopedia e Traumatologia dell'Italia Meridionale e Insulare 90 Congresso, Jun. 21-23, 2001, Paestum.

Petrini, et al., "Stabilizzazione Elastica," Patologia Degenerativa del Rachide Lombare, Oct. 5-6, 2001, Rimini.

Pupin, et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary, et al., "Cervical Spina Stabilization with Flexible, Multistrand Cable System," Techniques in Spinal Fusion and Stabilization, Hitchon et al., eds., 1995, pp. 79-81, Ch. 7, Thieme, New York.

Richards, et al., "The Treatment Mechanism of an Interspinous Process Implant for Lumbar Neurogenic Intermittent Claudication," SPINE, 2005, pp. 744-749, vol. 30, No. 7.

Scarfo, "Instability/Stenosis: Holistic Approach for Less Invasive Surgery," date unknown, University of Siena, Siena, Italy.

Schiavone, et al., "The use of disc assistance prostheses (DIAM) in degenerative lumbar pathology: Indications, Tecchnique, Results," Italian J. Spinal Disorders, 2003, pp. 213-220, vol. 3, No. 2.

Schlegel, et al., "The Role of Distraction in Improving the Space Available in the Lumbar Stenotic Canal and Foramen," SPINE, 1994, pp. 2041-2047, vol. 19, No. 18.

Sénégas, "Mechanical supplementation by non-rigid fixation in degenerative intervertebral lumbar segments: the Wallis system," Eur. Spine J., 2002, pp. S164-S169, vol. 11, Suppl. 2).

Sénégas, et. al., "Stabilisation lombaire souple," Instabilités Vertébrales Lombaires, Gastambide, ed., 1995, pp. 122-132, Expansion Scientifique Francaise, Paris, France.

Sénégas, "La Ligamentoplastie Inter Vertébrale Lombaire, Alternative à L'Arthrodèse," La Revue de Medécine Orthopédique, Jun. 1990, pp. 33-35, No. 20.

Sénégas, "La Ligamentoplastie Intervertébrale, Alternative à L'Arthrodése Dans Le Traitement Des Instabilités Dégénératives," Acta Othopaedica Belgica, 1991, pp. 221-226, vol. 57, Suppl. I.

Sénégas, "Rencontre," Maîtrise Orthopédique, May 1995, pp. 1-3, No. 44.

Sénégas, et al., "Le recalibrage du canal lombaire, alternative à la laminectomie dans le traitement des sténoses du canal lombaire," Revue de Chirurgie Orthopedique, 1988, pp. 15-22.

Serharn, et al., "Spinal Implants: Past, Present, and Future," 19th International Conference IEEE/EMBS Conference, Oct. 30-Nov. 2, 1997, pp. 2636-2639.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—modified CAD geometry and meshing," date unknown.

Taylor, et al., "Technichal and Anatomical Considerations for the Placement of a Posterior Interspinous Stabilizer", Lumbar Spine, pp. 466-475.

Taylor, et al., "Technical and Anatomical Consideration for the Placement of a Posterior Interspinous Stabilizer", Medtronic, 2004, pp. 3-11.

Taylor,, "Posterior Dynamic Stabilization using the DIAM (Device for Intervertebral Assisted Motion)".

Taylor, et al., "Analyse d'une expérience clinique d'un implant postérieur amortissant, "Rachis Revue de Pathologie Vertébrale, Oct./Nov. 1999, vol. 11, No. 4-5, Gieda Inter Rachis.

Taylor, et al., "Biomechanical requirements for the posterior control of the centers of rotation.", Swiss Spine Institute International Symposium: Progress in Spinal Fixation,, Jun. 21, 2002, pp. 1-2, Swiss Spine Institute, Berne, Switzerland.

Taylor, "Non-Fusion-Technologies of the posterior column: A new posterior shock absorber," International Symposium on Intervertebral Disc Replacement and Non-Fusion-Technology, May 3-5, 2001, Spine Arthroplasty.

Taylor, et al., "Surgical Requirement for the Posterior Control of the Rotational Centers," date unknown.

Taylor, "Présentation à un an d'un dispositif amortissant d'assistance discale," 5èmes journées Avances & Controverses en pathologie rachidienne, Oct. 1-2, 1998, Faculté Libre de Mé decine de Lille.

Technica Operatoria Per IL Posizionamento Della Protesi DIAM, date unknown, pp. 1-3.

The Posterior Intervertebral Implant of Professor J. Senegas, date unknown.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville, et al., "Experimental lumbar instability and artificial ligament," Eur. J. Orthop. Surg. Traumatol, 2000, pp. 167-176, vol. 10.

Voydeville, et al., "Lumbar Instability Treated by Intervertebral Ligamentoplasty with Smooth Wedges," Orthopédie Traumatologie, 1992, pp. 259-264, vol. 2, No. 4.

Wallis Operative Technique: Surgical Procedure for Treatment of Degenerative Disc Disease (DDD) of Lumbar Spine, date unknown, pp. 1-24, Spine Next, an Abbott Laboratories Company, Bordeaux, France.

Wiltse, et al., "The Treatment of Spinal Stenosis," Clinical Orthopaedics and Related Research, Urist, ed., Mar.-Apr. 1976, pp. 83-91, No. 115.

Wisneski, et al. "Decompressive Surgery for Lumbar Spinal Stenosis," Seminars in Spine Surgery, Wiesel, ed., Jun. 1994, pp. 116-123, vol. 6, No. 2.

Zucherman, et al., "Clinical Efficacy of Spinal Instrumentation in Lumbar Degenerative Disc Disease," SPINE, Jul. 1992, pp. 834-837, vol. 17, No. 7.

International Search Report, completed Dec. 5, 2006 for International Application No. PCT/US2006/030614, filed Aug. 3, 2006.

\* cited by examiner

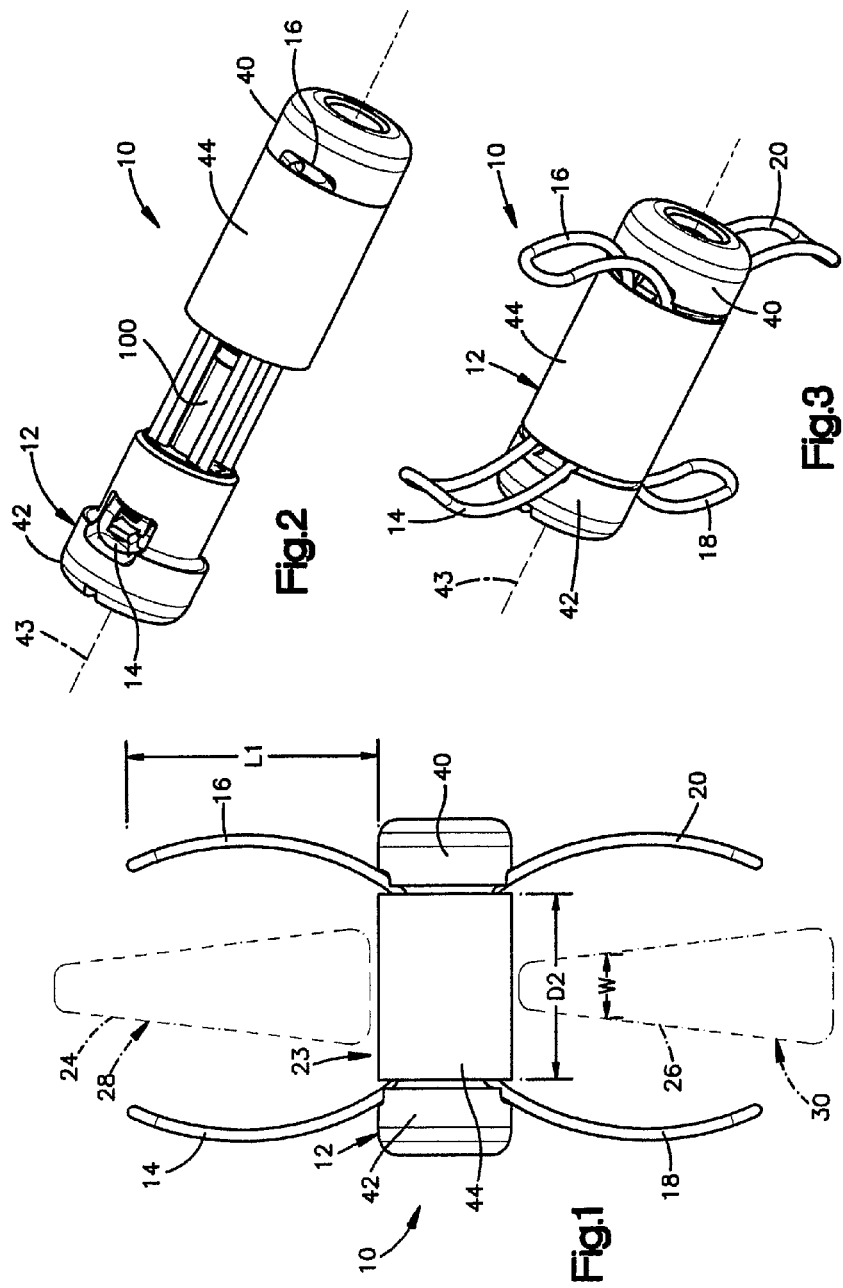

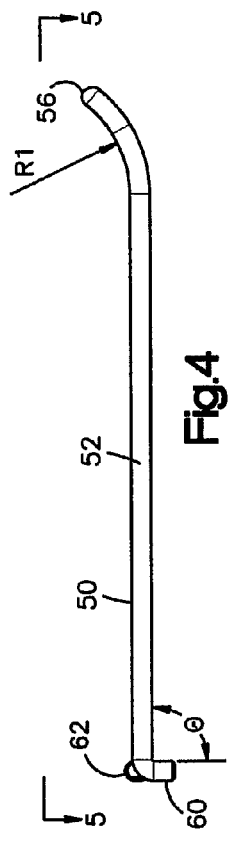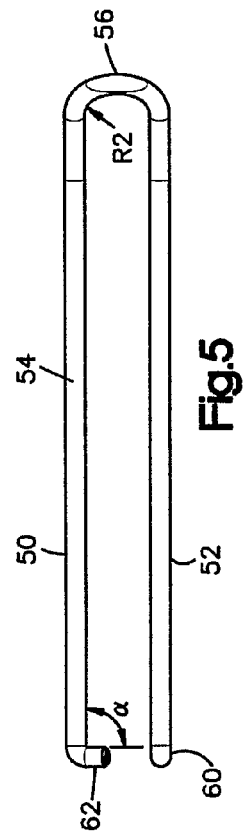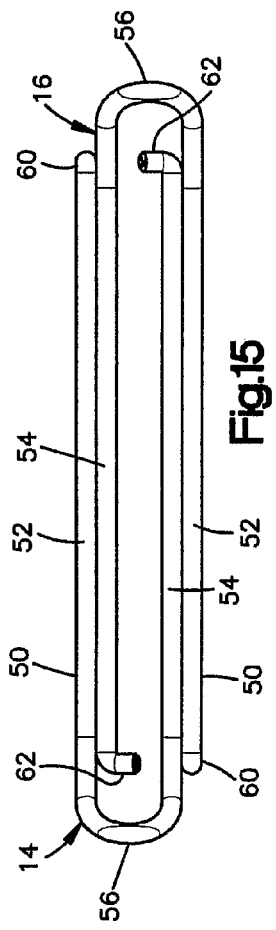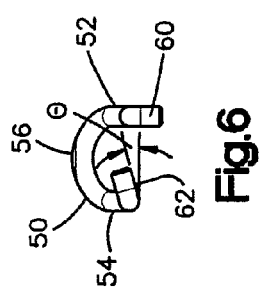

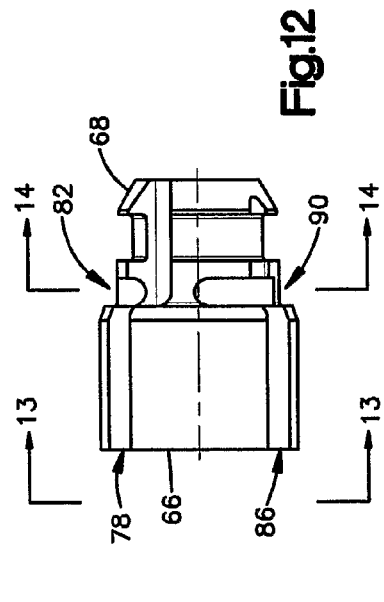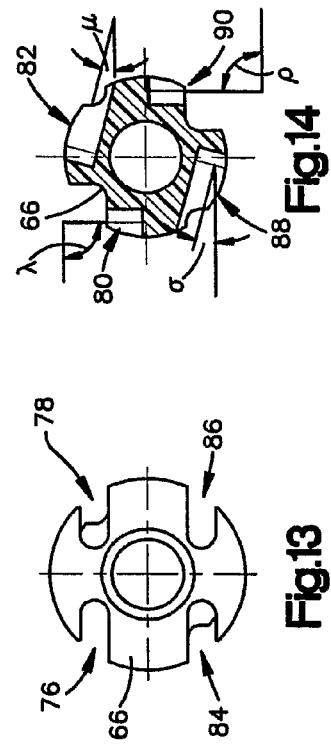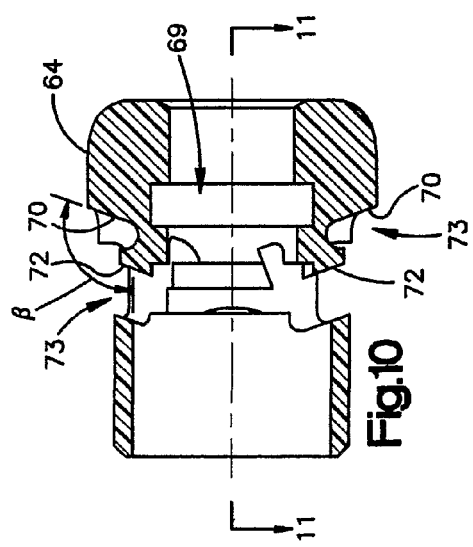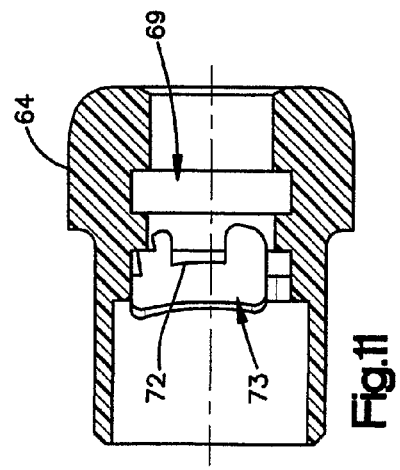

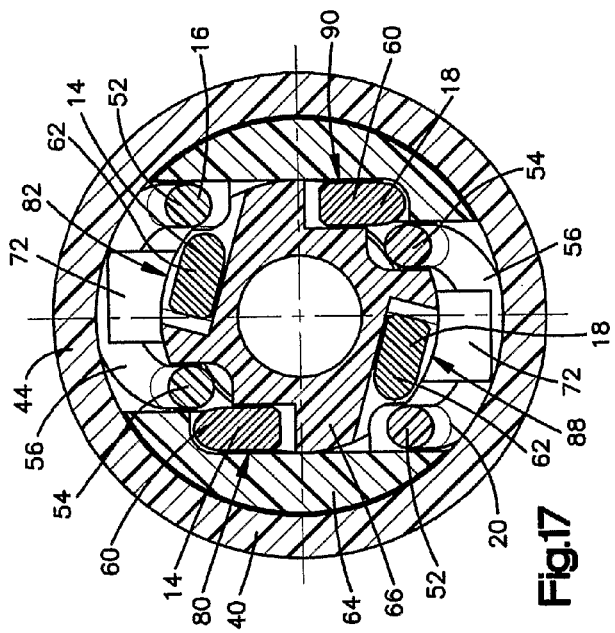
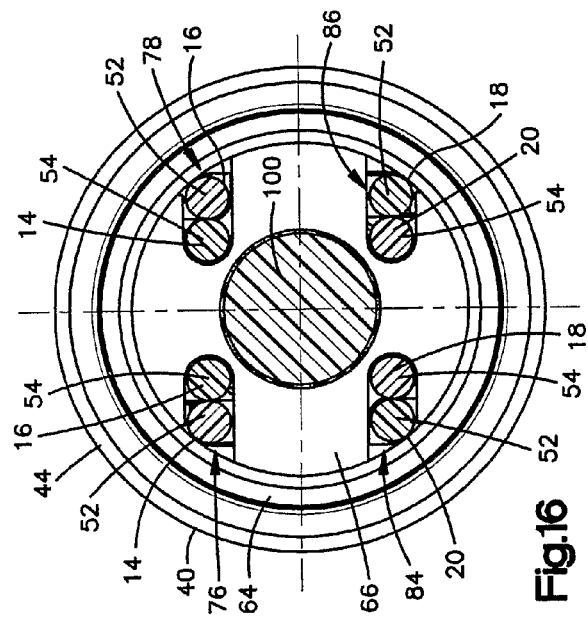
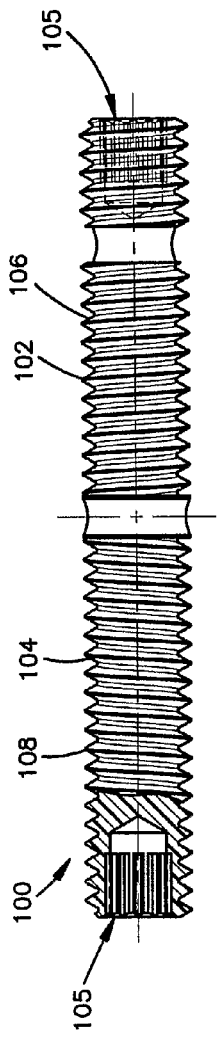

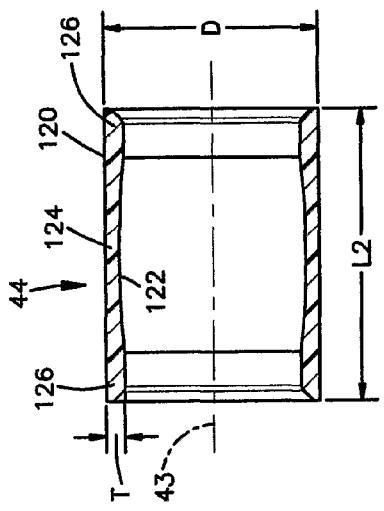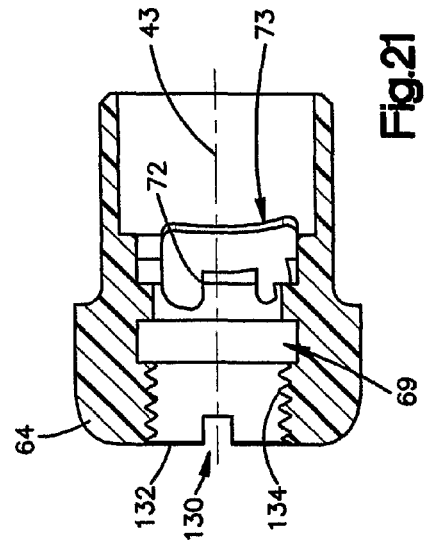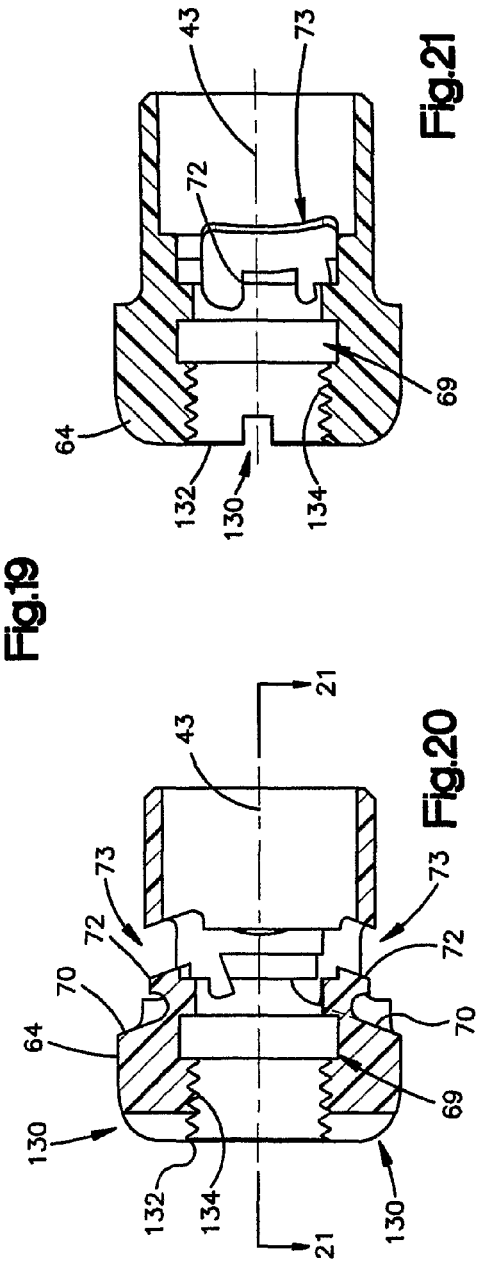

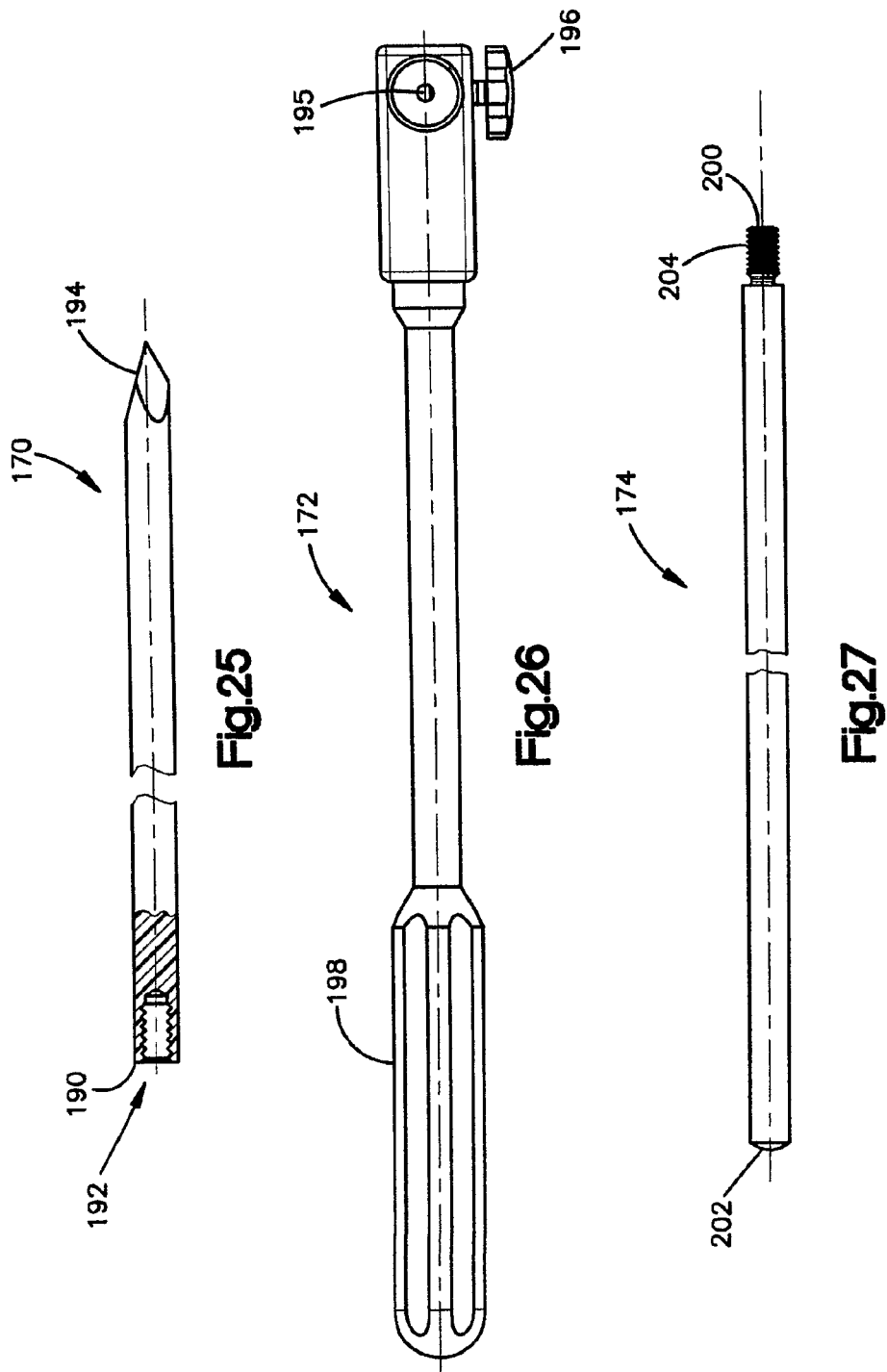

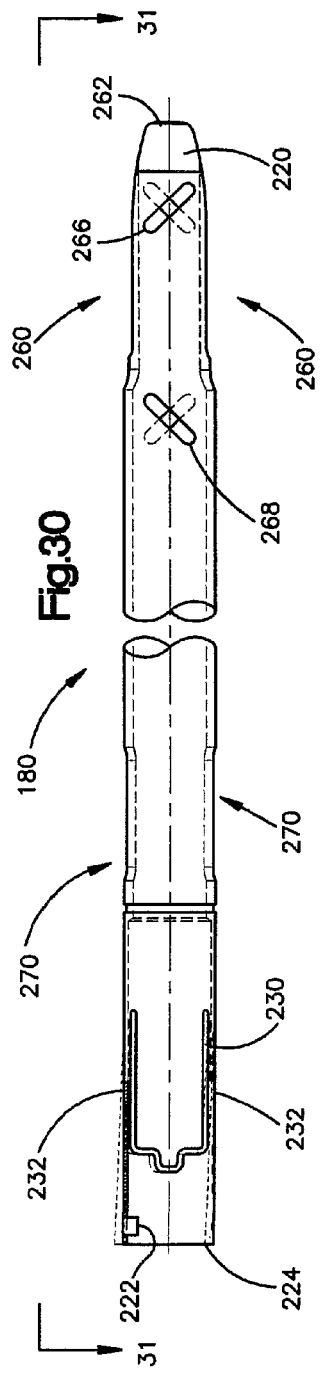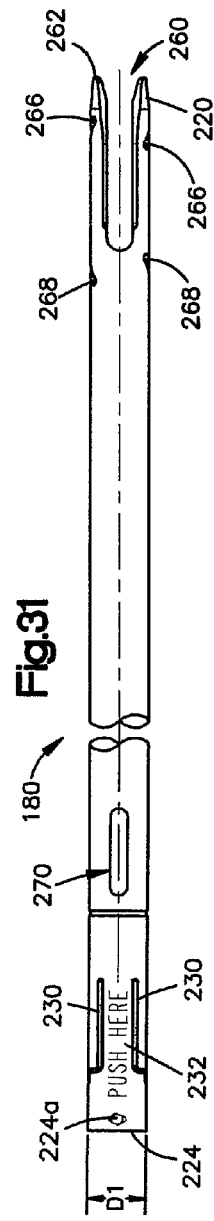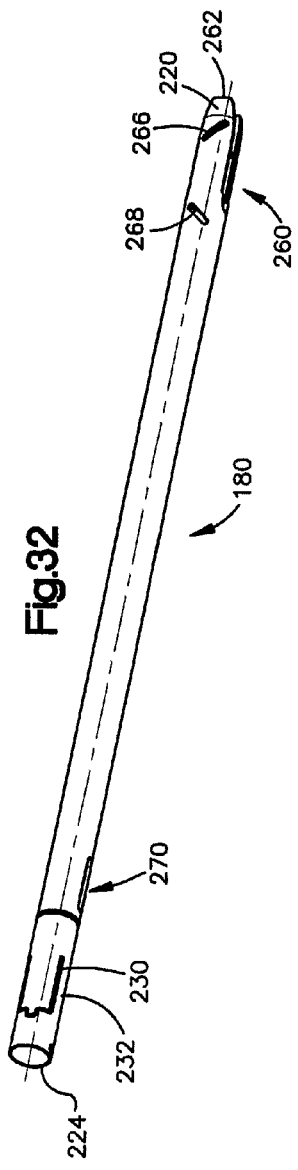

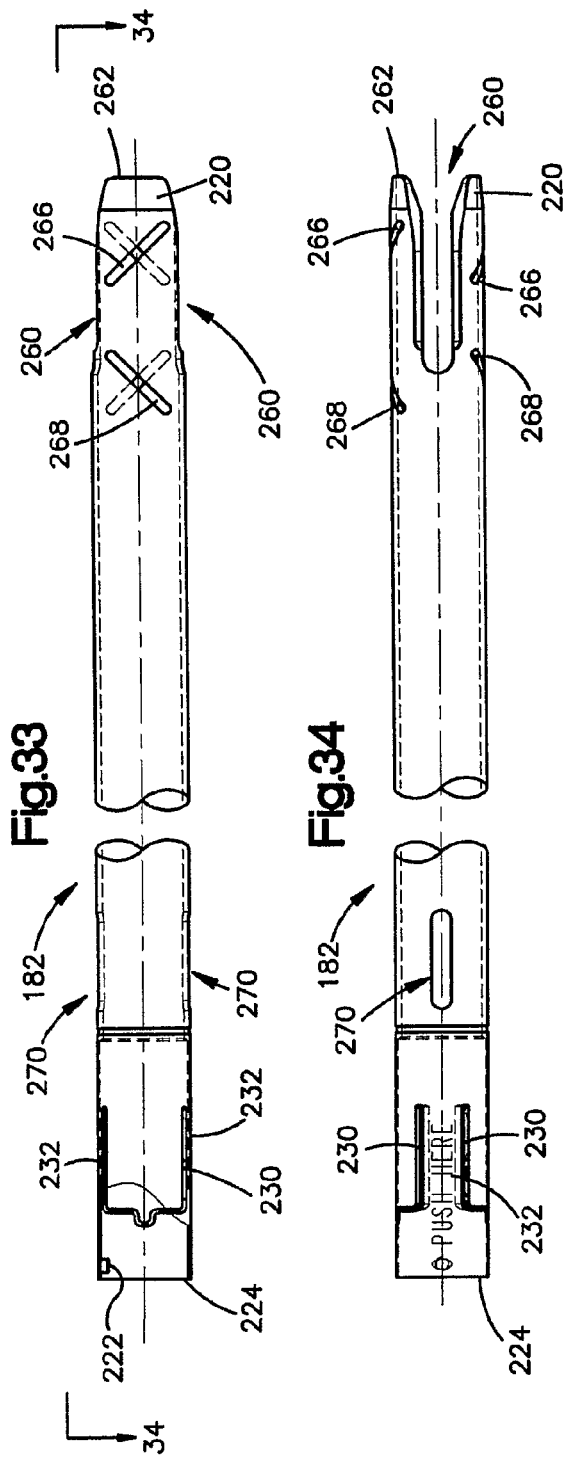

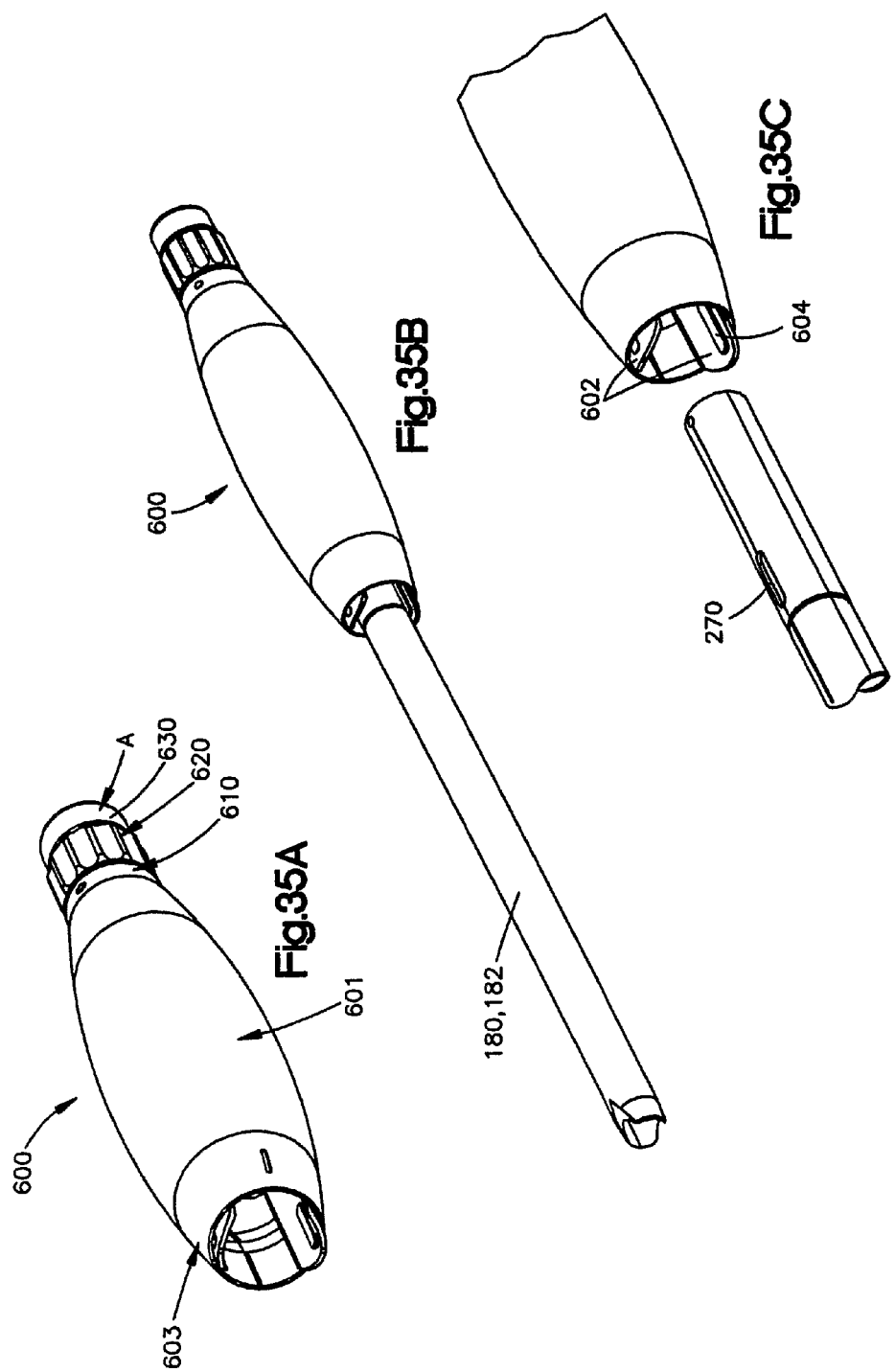

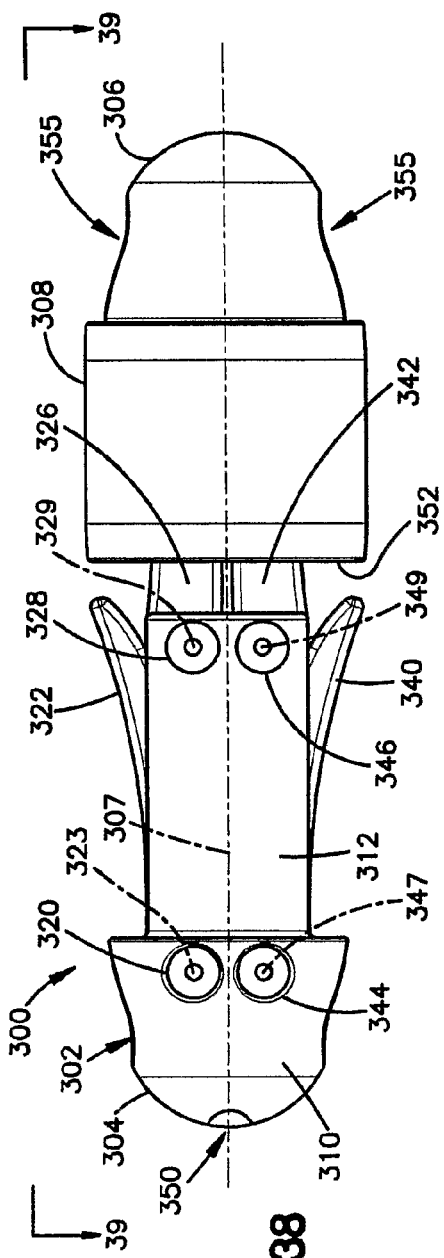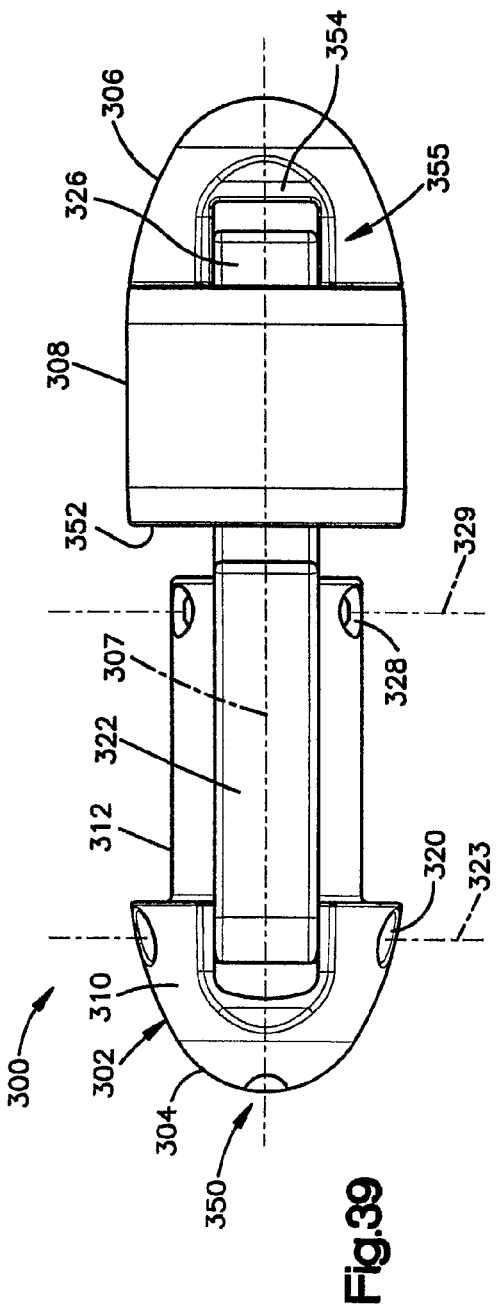

PRONGED HOLDER FOR TREATING SPINAL STENOSIS

RELATED APPLICATIONS

This application is a National Stage Entry of Application Number PCT/US2006/030614 filed Aug. 3, 2006, which claims priority from provisional application No. 60/795,883 filed Apr. 27, 2006. This application is also a continuation-in-part of U.S. application Ser. No. 11/198,393 filed Aug. 5, 2005, now U.S. Pat. No. 7,753,938. Each of these applications are herein incorporated by reference in their entirety.

TECHNICAL FIELD

The present invention relates to an apparatus and method for stabilizing the human spine and, more specifically, to an implant for insertion between adjacent vertebrae.

BACKGROUND

A human vertebrae has a rearwardly projecting portion known as a spinous process. Bending of the spine can cause the spinous processes of adjacent vertebrae to be moved toward each other. This constricts the space in the spinal canal and foramina and, thus, may cause pain. Such constriction, which is known as stenosis, can be treated by the use of an implant in the space between adjacent spinous processes.

Some current implants are made of separate pieces which require insertion from opposite sides of the spine and in a posterior approach necessitate rather wide openings into a patient, cutting both left and right thoracolumbar fascia as well as stripping the multifidus muscles from their attachments. It is desirable to provide an implant for insertion between the spinous processes of adjacent vertebrae which can be inserted through a single opening in a minimal invasive approach and may be held firmly in position between the vertebrae.

SUMMARY

The device of the present invention may include a body portion having a first end portion, a second end portion and a sleeve which may be positioned between the first and second end portions. The device may be sized and configured to fit between the spinous processes of two adjacent vertebrae. The sleeve may be a single piece of material or may comprise multiple components which may be made of materials having different properties (e.g., different modulus of elasticity). The device may have at least two retainers, which may be positioned within the body portion and may move between a deployed position and a retracted position. The device may also have a connector which may join the first and second end portions.

An actuation tool (e.g., a screwdriver) may be used to rotate the connector. Rotation of the connector may move the first and second end portions towards each other. As the first and second end portions are moved toward each other, the retainers may be deployed from the device. In the deployed position, the retainers may extend outward from the body portion and may be positioned on opposite sides of at least one spinous process of a vertebrae. In a preferred embodiment, the device may have four retainers for engaging opposite sides of two spinous processes of adjacent vertebrae. Such retainers may hold the implant in position relative to the spine.

In an alternative embodiment, the device includes a body portion having a first end portion, a second end portion and a sleeve which may be positioned between the first and second end portions. The first end portion may have an elongated member extending therefrom and two or more retainers may be operably associated with the first end portion and elongated member. In a preferred embodiment, two retainers may be pivotably connected to the first end portion and two retainers may be pivotally connected to the elongated member. A connector may be positioned between the end portions such that rotation of the connector may draw the end portions together. The second end portion may have one or more opening through which a retainer may pass. As the end portions move together, the retainers connected to the elongated member may move through the opening in the second end portion and extend away from the body portion. Moreover, the retainers connected to the first end portion may move against the sleeve and extend away from the body portion. The body portion and first and second end portions may be situated such that spinous processes of adjacent vertebrae may be positioned between the retainers. In another embodiment, at least one retainer, but preferably two retainers may be pivotably connected to each end portion. As the end portions move together, the retainers may move against the sleeve and may extend from the body portion.

An apparatus for treating spinal stenosis may comprise an implant body structure configured to fit between spinous processes of two adjacent vertebrae, at least two retainers operably associate with the body structure, and a mechanism operative to move the two retainers from a retracted position to a deployed position extending outward from the body structure beside the spinous process of one of the two adjacent vertebrae. The mechanism may be a screw. The mechanism may be contained within the body structure. The body structure may have a first end and a second end and the two retainers may extend from opposite or adjacent ends of the body structure when in the deployed position.

The apparatus may further comprise a third and fourth retainer operably associated with the body structure, the mechanism being operative to drive the third and fourth retainers from respective retracted positions to respective deployed positions extending outward from the body structure on opposite sides of the spinous process of the other of the two adjacent vertebrae. The mechanism may comprise an elongated connector having an axis and mounted within the body structure and the body structure may comprise first and second body end portions spaced apart along the axis; wherein the mechanism is operative to move the first and second body end portions axially toward each other such that the at least two retainers move from the retracted position to the deployed position under the influence of the first and second body end portions as they are moved axially toward each other. The retainer may be mounted on the first body end portion by a hinge. At least one retainer may be fixed to the first body end portion to move axially with the first body portion and slide axially with respect to the second body end portion upon movement of the first body end portion axially toward the second body end portion; wherein the second body portion is configured to deflect and guide that one retainer to move the retainer from the retracted position to the deployed position.

The retainers may be a wire which extends between the first body end portion and the second body end portion. The wire of at least one retainer may be generally U-shaped and may have free ends, wherein the free ends preferably are fixed to the first body end portion to move with the first body end portion as the first body end portion moves axially relative to the second body end portion. The first body end portion and second body end portion may each have a cam surface for deflecting the wire. The mechanism may comprise an elongated connector having a longitudinal axis, a screw thread in a first direction engaged with the first body end portion, and an oppositely extending screw thread in a second direction engaged with the second body end portion.

The body structure may further include a sleeve located axially between the first and second body end portions. The sleeve may be capable of rotating relative to the first and second body end portions under forces applied from the spinous processes of the two adjacent vertebrae. The sleeve also may be capable of deflecting under forces applied from the spinous processes of the two adjacent vertebrae. The sleeve may have opposite end sections and a central section that may be thinner than the opposite end sections. The sleeve may have a first sleeve component formed of a material with a modulus of elasticity and a second sleeve component formed of a material with a different modulus of elasticity. The mechanism may be operative to retract the retainers from the deployed positions to the retracted positions.

The body structure may comprise a first end portion and a second end portion, the mechanism may comprise an elongated connector having a longitudinal axis and at least a portion of which may have external screw threads, the connector may be configured for rotation, wherein the first end portion and second end portion each have internal threads and are mounted on the elongated connector, and each retainer may comprise a generally U-shaped wire having two free ends, wherein the two free ends of a first retainer is fixed to the first end portion and the two free ends of a second retainer are fixed to the second end portion, wherein upon rotation of the connector in a first direction, the first and second end portions move axially along the connector closer together and deploy the retainers at an angle with respect to the axis of the connector.

In another embodiment, the implant may comprise a body structure having a longitudinal axis configured to be placed between spinous processes of two adjacent vertebrae, and having a peripheral middle portion configured to move under forces applied from the spinous processes of the two adjacent vertebrae; and at least two retainer members configured to move from a retracted position wherein the retainer members are generally aligned with the axis and a deployed position wherein the retainer members generally extend from the body structure at an angle with respect to the axis and into a location beside a spinous process on a vertebrae. The peripheral middle portion of the body structure may be configured to rotate relative to the retainers under forces applied from the spinous processes of the two adjacent vertebrae. The spinal implant may further comprise first and second end portions, wherein the first end portion has an extension with two pivot connections and the second end portion has two guide windows. The at least two retainer members may have a proximal end and a distal end, wherein the distal end of each retainer is pivotally connected to a pivot connection and wherein the at least two retainers may be sized and configured such that the proximal ends of the retainers pass through the guide windows when the end portions are moved towards each other. The spinal implant may further comprise a third and fourth retainer having distal and proximal ends, wherein the first end portion has two pivot connections and the distal end of each of the third and fourth retainer is pivotally connected to a pivot connection of the first end portion.

The spinal implant may be part of a system which includes a screwdriver configured to actuate the mechanism to drive the retainers from the retracted positions to the deployed positions when the body structure is located between the spinous processes of the two adjacent vertebrae.

A system for maintaining the space of vertebrae may be provided which may comprise a body structure configured to be placed between spinous processes of two adjacent vertebrae, and further having at least two retainers configured in a deployed position to project outward from the body structure beside the spinous process of one of the two adjacent vertebrae; and a tube configured to receive the implant body structure, wherein the tube has at least one opening through which the retainers are movable to the deployed position. The opening for the retainers may be a slot. The tube may have a tapered portion configured to dilate soft tissue and distract the spinous processes of the two adjacent vertebrae. The opening for the retainers may extend through the tapered portion of the tube. The tube may further have visual markers that are offset from the opening on opposite sides of the tube such that the visual markers move into a predetermined orientation relative to each other upon rotation of the tube to a position in which the opening has a predetermined orientation relative to the deployed position of the retainer.

A kit for treating spinal stenosis may be provided which comprises a plurality of differently sized spinal implants, each implant including an implant body structure configured to fit between spinous processes of two adjacent vertebrae; at least two retainers operably associated with the body structure; and a mechanism operative to move the retainers from a retracted position to a deployed position extending outward from the body structure beside the spinous process of one of the two adjacent vertebrae. The kit may further comprise a plurality of differently sized tubes configured to distract the spinous processes of the two adjacent vertebrae in succession as each larger tube is received over the next smaller tube, with each tube sized for a corresponding one of the spinal implants to slide through the passageway provided by the tube when any smaller tubes have been removed from within the tube. The tubes preferably are configured to limit movement of each larger tube over the next smaller tube such that inner end portions of the tubes overlap in a predetermined manner when the tubes are nested together. Each larger tube may have a stop member configured to move into abutment with the next smaller tube. Each larger tube may be configured to be deflected to a condition in which the respective stop member is displaced from abutment with the next smaller tube. Each larger tube may have slots defining opposed portions of the tube that are deflectable inwardly of the tube.

In one embodiment, a kit or system of instruments for insertion of a spinal implant may comprise a tube having a passageway configured for the body structure of the implant to slide to an inner end portion of the tube; and an implant holder configured to engage the body structure, to move the body structure through the tube, and to engage the tube to limit movement of the body structure at the inner end portion of the tube. The implant holder preferably is configured to attach to the body structure outside the tube, and to detach from the body structure inside the inner end portion of the tube. The tube may be one of a plurality of differently sized tubes, each of which is configured for an implant body structure of a corresponding size to slide to the inner end portion of the tube; and the implant holder is a single device configured to engage each body structure individually, to move each body structure through a corresponding one of the differently sized tubes, and to engage each of the differently sized tubes individually to limit movement of the body structure at the inner end portion of the tube.

A device for holding a surgical instrument or implant comprising a body having a proximal end, a distal end and a passageway positioned therethrough; an instrument engagement device positioned in the passageway, the engagement device having at least two prongs moveable relative to each other so that the surgical instrument is held therebetween; and a knob operably associated with the at least two prongs so that movement of the knob causes movement of the at least two prongs relative to each other, wherein at least one prong has at least one ridge for engaging at least one slot of the surgical instrument. The knob may comprise a locking mechanism which is rotatable relative to the body so as to fix the position of the prongs relative to each other. The prongs may move away from each other when the knob is pushed towards the distal end of the body and wherein the prongs are spring loaded so that the prongs move towards each other when the knob is released.

A method for treating spinal stenosis is also provided which comprises (i) providing an implant having a body structure having first and second end portions and an intermediate portion between the first and second end portions, at least two retainers operably associated with the end portions and positioned within the body structure in a retracted position, and a connector operably connecting the first and second end portions; (ii) inserting the implant between spinous processes of adjacent vertebrae; and (iii) actuating the connector to move the ends portions relative to each other such that the retainers move between the retracted position and a deployed position, wherein, in the deployed position, the retainers extend outward from the body structure and engage at least one spinous process.

An alternative method for treating spinal stenosis may comprise (i) providing an implant having a body structure having first and second end portions, at least two retainers operably associated with the end portions and positioned within the body structure in a retracted position; and a connector operably connecting the first and second end portions, (ii) providing at least one dilator and at least one tube for insertion into the body, wherein the at least one tube has a passageway therethrough; (iii) inserting the at least one dilator laterally into the body between adjacent spinous processes; (iv) inserting the at least one tube over the at least one dilator; (v) removing the at least one dilator from the body, leaving the at least one tube between adjacent spinous processes; (vi) inserting the implant through the at least one tube and in between adjacent spinous processes; and (vii) actuating the connector to move the ends portions relative to each other such that the retainers move between the retracted position and a deployed position, wherein, in the deployed position, the retainers extend outward from the body structure. The method may further comprise inserting a guide wire into the body. The method may further comprise positioning at least one of the dilators and the at least one tube over the guide wire. The step of inserting the at least one dilator laterally into the body may comprise distracting adjacent spinous processes. Alternatively, the step of inserting the at least one tube laterally into the body over the at least one dilator may not further distract the spinous processes. The step of inserting the implant through the at least one tube may comprise inserting the implant laterally into the body.

In one method of inserting the spinous spacer, an incision may be made in the side of a patient. A guide wire may be inserted through the incision and in between adjacent spinous processes. An extension may be operably connected to the guide wire to extend the length of the wire. A dilator may be inserted over the guide wire and may retract tissue and distract the spinous processes. Thereafter, sequentially larger tubes may be positioned over the dilator, further dilating tissue and distracting adjacent spinous processes. Once the largest tube is in position, the guide wire, dilator and any other smaller tubes may be removed from the body leaving the largest tube in position. An implant holder may be attached to the spinous spacer in an expanded or elongated configuration and may be used to insert the device down the tube in between the vertebrae. An actuation tool may be positioned through the implant holder and may engage the connector. The implant holder may be held stationary while the actuation tool may be rotated. In this way, the end portions of the spinous spacer may move towards each other and the retainers may deploy from the body portion and through slots in the tube. Once the retainers are deployed and the device is positioned between adjacent spinous processes, the implant holder, actuation tool and outer tube may be removed from the body.

BRIEF DESCRIPTION OF THE DRAWINGS

The spinous spacer and the method of use and insertion are explained in even greater detail in the following exemplary drawings. The spinous spacer, and its method of operation and use may be better understood by reference to the following drawings, wherein like references numerals represent like elements. The drawings are merely exemplary to illustrate the structure, operation and method of use of the spinous spacer and certain features that may be used singularly or in combination with other features and the invention should not be limited to the embodiments shown.

FIG. 1 is a side view of an exemplary embodiment of an implant of the present invention positioned between adjacent spinous processes;

FIG. 2 is a perspective view of an exemplary embodiment of the implant of FIG. 1 in a first configuration;

FIG. 3 is a perspective view of an exemplary embodiment of the implant of FIG. 1 in a second configuration;

FIG. 4 is a side view of an exemplary embodiment of a retainer of the implant of FIG. 1;

FIG. 5 is a top view of an exemplary embodiment of the retainer of FIG. 4 along line 5-5;

FIG. 6 is an end view an exemplary embodiment of the retainer of FIG. 4;

FIG. 10 is a cross-sectional view of an exemplary embodiment of an end portion of the implant of FIG. 2;

FIG. 11 is a cross-sectional view of the end portion of FIG. 10 along line 11-11;

FIG. 12 is a side view of an exemplary embodiment of an inner portion of the implant of FIG. 2;

FIG. 13 is an end view of the inner portion of FIG. 12 along line 13-13;

FIG. 14 is a cross-sectional view of the inner portion of FIG. 12 along line 14-14;

FIG. 15 is a top view of an exemplary embodiment of a pair of retainers of FIG. 4;

FIG. 16 is a partial cross-sectional view of the implant of FIG. 2;

FIG. 17 is another cross-sectional view of the implant of FIG. 2;

FIG. 18 is a side view of an exemplary actuation mechanism as shown in FIG. 7;

FIG. 19 is a cross-sectional view of an exemplary sleeve of the implant of FIG. 2;

FIG. 20 is a cross-sectional view of the end portion of FIG. 10;

FIG. 21 is a cross-sectional view of the end portion of FIG. 20 along line 21-21;

FIG. 25 is a partial cross-sectional side view of an exemplary embodiment of a guide wire of the present invention;

FIG. 26 is a side view of an exemplary embodiment of a guide wire holder of the present invention;

FIG. 27 is a side view of an exemplary embodiment of an extension for the guide wire FIG. 25;

FIG. 30 is a side view of an exemplary embodiment of an insertion device of the present invention;

FIG. 31 is a top view of the insertion device of FIG. 30 along line 31-31;

FIG. 32 is a perspective view of the insertion device of FIG. 30;

FIG. 33 is a side view of exemplary embodiment of another insertion device of the present invention;

FIG. 34 is a top view of the insertion device of FIG. 33 along line 34-34;

FIG. 35 is a perspective view of the insertion device of FIG. 33;

FIG. 35A is a perspective view of an exemplary embodiment of a handle;

FIG. 35B is a perspective view of the handle of FIG. 35A and an insertion device;

FIG. 35C is an enlarged view of a portion of FIG. 35B;

FIG. 38 is a side view of an exemplary embodiment of an alternative implant in a first configuration;

FIG. 39 is a top view of the implant of FIG. 38 along line 39-39;

DESCRIPTION

Figure 7:
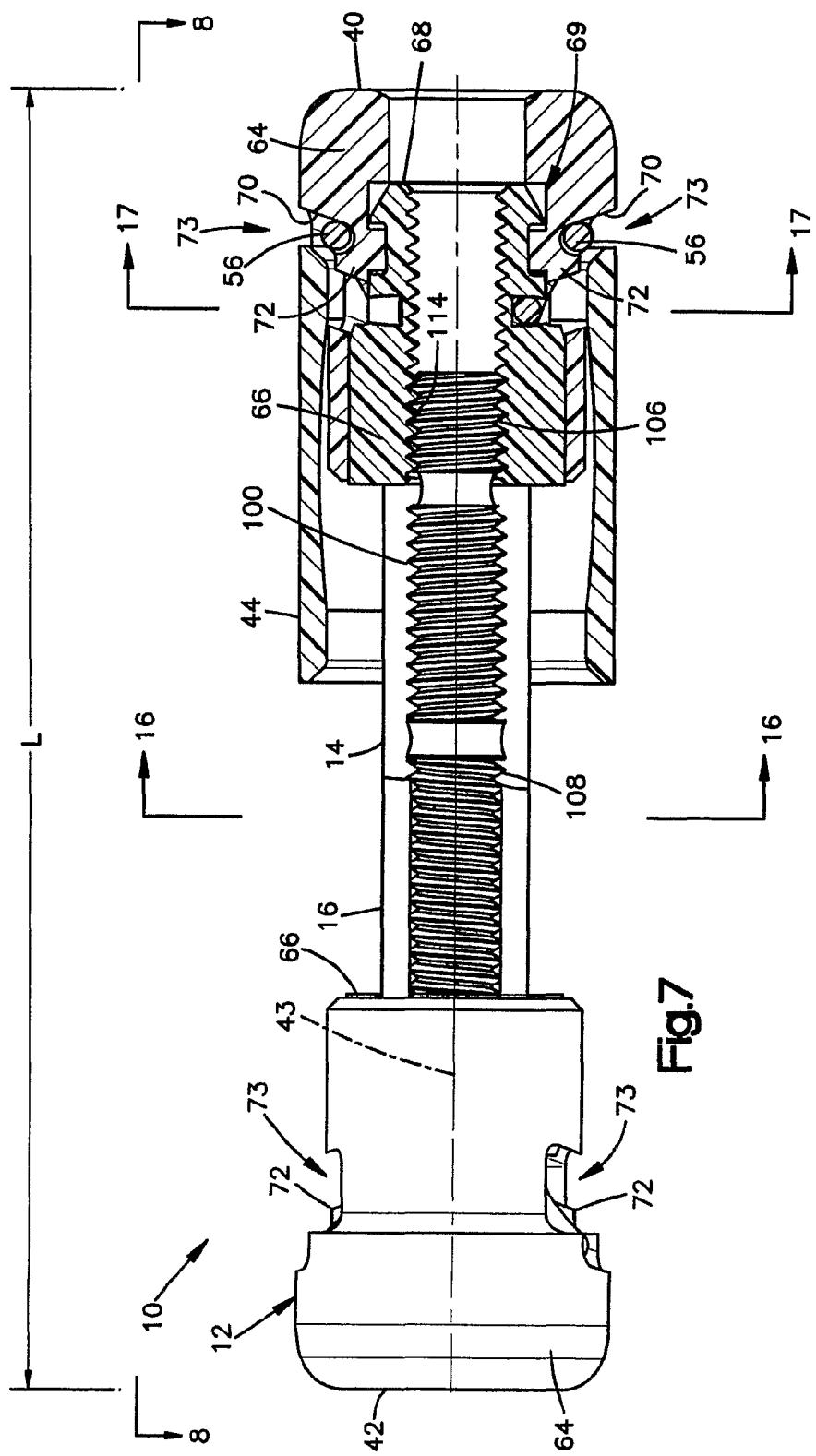
FIG. 7 is a side view showing a partial cross-section of the implant of FIG. 2.

As shown in FIG. 1, the device 10, referred to herein as a spinous spacer, may include a body portion 12, a first set of retainers 14 and 16, and a second set of retainers 18 and 20.

The body portion 12 may have a sleeve 44, a first end portion 40 and a second end portion 42. The first and second end portion 40, 42 may be moveable relative to the sleeve 44. It should, however, be understood that those of ordinary skill in the art will recognize many modifications and substitutions which may be made to various elements of the present invention, and that the embodiments illustrated and described are merely exemplary.

The device 10 may be positioned in between spinous processes of adjacent vertebrae 28,30 for treating, for example, spinal stenosis. The spinous spacer 10 may be one member of a set/kit of implants 10 which have different dimensions which takes into account the differing anatomy of patients. Although the device 10 is described herein as being used in connection with treating spinal stenosis, one of ordinary skill in the art will readily appreciate that the device may be used in any other part of the body, including specifically the spine where occupying space between portions of the spine and vertebrae may be desirable. Thus, the location and/or surgical procedure is not intended to be limiting in any way.

The first end portion 40, second end portion 42 and sleeve 44 may be any shape, for example, round, oval or polygonal. Moreover, the retainers 14, 16, 18 and 20 may be straight, concave, convex or any other shape so long as a vertebral body (e.g. spinous process) may be positioned between or held by pairs of retainers 14, 16 and 18, 20. The body portion 12, including the first and second end portions 40, 42 and sleeve 44, as well as the retainers 14, 16, 18 and/or 20 may be made of any suitable material, preferably biocompatible material, such as metal (e.g., stainless steel, titanium, aluminum, an alloy of two or more metals), plastic, polymer, rubber, ceramic, natural body tissue (e.g., bone) or a composite material (i.e., made up of two or more materials). Various factors may be considered when determining the material used to make the elements of the device 10, including but not limited to, for example, ability to withstand sterilization, ability to withstand forces exerted thereon, weight, durability, and the ability to grip the device 10, particularly with latex gloves. With regard to the retainers 14, 16, 18 and 20, factors may also include the ability to elastically and plastically bend, and/or deform the retainers 14, 16, 18 and 20 as well as the ability to retain shape after deformation. The body portion 12 and/or any other component of the device 10 may be radiolucent or radioopaque. In embodiments where the body portion 12 or other components may be radiolucent, radio-opaque markers (not shown) may be incorporated into or attached to the body portion 12 or other components. The radio-opaque markers may assist a surgeon in properly aligning the body portion 12 or other components relative to a patient's anatomy.

The retainers 14, 16, 18 and 20 may be sized and configured similar to each other and may pass through or under the sleeve 44, first portion 40 and second portion 42. As shown in FIGS. 4-6, each retainer 14, 16, 18 and 20 may be an elongated structure such as, for examples, a wire 50. The wire 50 may have a gauge of between about 0.01 inches and about 0.1 inches. Moreover, the wire 50 may have a length of between about 1.0 inch and about 10 inches before being formed into retainer 14, 16, 18 and 20. The wire 50 may be generally U-shaped with a curved portion 56 and arms 52, 54, which may extend from the curved portion 56. The curved portion 56 may be curved or bent in more than one plane as illustrated in FIGS. 4, 5 and 6. As shown in FIG. 4, the curved portion 56 may have a radius of curvature R1 of, for example, between about 0.1 inches and about 1.0 inch, more preferably, between about 0.1 inches and about 0.5 inches and, most preferably, between about 0.15 inches and about 0.2 inches. As shown in FIG. 5, the curved portion 56 may have a radius of curvature R2 of, for example, between about 0.01 inches and about 1.0 inch, more preferably, between about 0.05 inches and about 0.5 inches and, most preferably, between about 0.05 inches and about 0.1 inches.

Furthermore, as illustrated in FIGS. 4 and 6, an end 60 of the arm 52 may be bent in a first direction at an angle θ (e.g., about 90 degrees) relative to the arm 52. The end 62 of the arm 54 may be bent in a second direction, which may be the same or different direction as the first direction and which may be at an angle α (e.g., about 90 degrees) relative to the arm 54. In one embodiment, the end 62 may also be bent at an angle Θ (e.g., about 15 degrees) (FIG. 6) towards the arm 52. The ends 60 and 62 may be bent at angles other than about 90 degrees relative to arms 50, 52, respectively, or may have no bend at all. End portions 60 and 62 of each retainer 14, 16, 18 and 20 may be operably connected to an end portion 40, 42. Moreover, the curved portions 56 of each retainer 14, 16, 18 and 20 may be slidably associated with, retained by, guided by or connected to the other end portion 40, 42.

Figure 8:
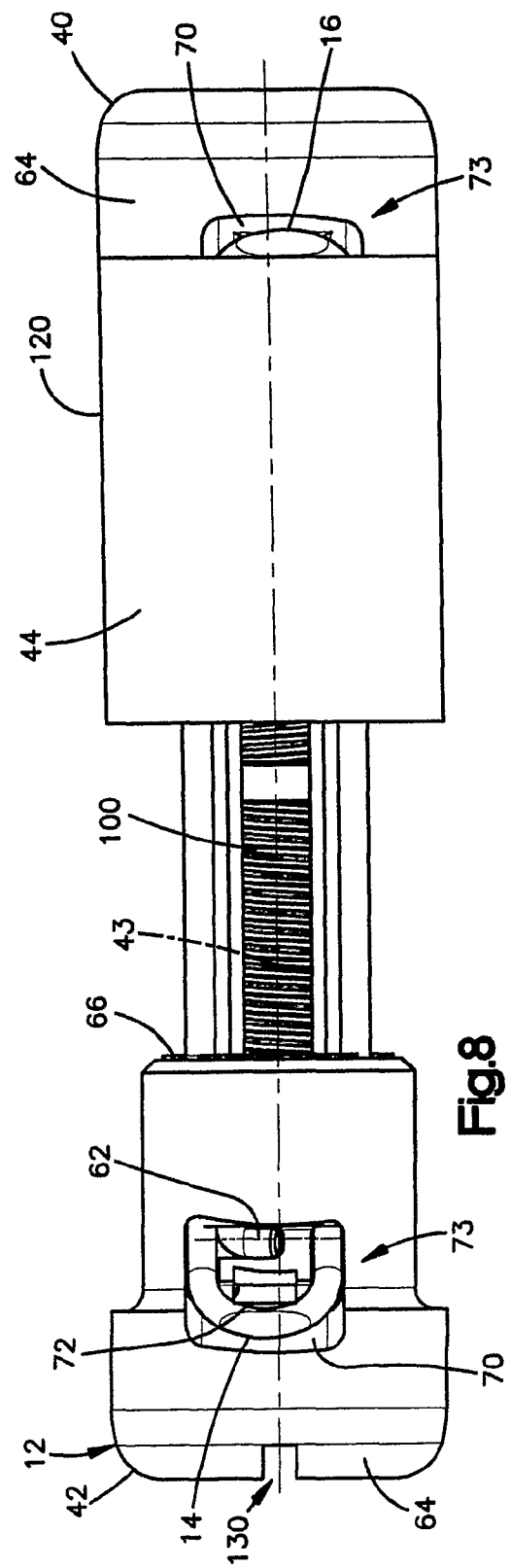
FIG. 8 is a side view of the implant of FIG. 7 along line 8-8.

As shown in FIGS. 7 and 8, the first end portion 40 may comprise an end cap 64 and an inner portion 66, each of which may have a generally cylindrical configuration and which may be centered on the axis 43. An end 68 of the inner portion 66 may be received in a groove 69 within the end cap 64 so that the inner portion 66 and the end cap 64 may be connected together. The end 68 may have a conical configuration; however, those skilled in the art will appreciate that other shapes may be used so long as the end 68 may be held in the end cap 64.

As shown in FIGS. 10 and 11, the end cap 64 may have first and second cam surfaces 70, and first and second teeth 72 proximate the cam surfaces 70. The cam surfaces 70 may have an angle β of, for example, between about 90 degrees and about 160 degrees, more preferably, between about 100 degrees and about 135 degrees and, most preferably, between about 105 degrees and about 115 degrees. The teeth 72 and cam surfaces 70 may be located within diametrically opposed openings 73 in the end cap 64.

Moreover, as shown in FIGS. 12, 13 and 14, the inner portion 66 may have a first and second upper slot 76, 78, respectively. A notch 80 at the end of the first upper slot 76 may extend at an angle λ (e.g., about 90 degrees) relative to the slot 76 (e.g., a downward angle) and a notch 82 at the end of the second upper slot 78 may extends at an angle μ (e.g., about 15 degrees) relative to the slot 78 (e.g., upward and toward the first upper slot 76). The angle of the notch 80 relative to the slots 76 may correspond to the angle θ of end 60 of the retainers 14, 16, 18 and 20. The angle of the notch 82 relative to the slots 78 may correspond to the angle Θ of the end 62 of the retainers 14, 16, 18 and 20. The inner portion 66 may also have first and second lower slots 84 and 86, which may have notches 88 and 90, respectively. The notch 88 at the end of the first lower slot 84 may extend at an angle σ (e.g., about 15 degrees) relative to the slot 84 (e.g., notch 88 may be angled downward and away from the second lower slot 86) and the notch 90 at the end of the lower slot 86 may extends at an angle ρ (e.g., about 90 degrees) relative to the slot 86 (e.g., an upward angle). The angle of the notch 88 relative to the slots 84 may correspond to the angle Θ of the end 62 of the retainers 14, 16, 18 and 20. The angle of the notch 90 relative to the slots 86 may correspond to the angle θ of end 60 of the retainers 14, 16, 18 and 20.

As illustrated in FIGS. 15 and 16, at least a portion of the retainers 14 and 16 may be positioned beside each other and generally inside the body portion 12 when in the deployed or undeployed position. As shown in FIG. 16, the arms 52 and 54 of the retainers 14 and 16 may be received in the first and second upper slots 76 and 78 in the inner portion 66 of the first end portion 40. The ends 60 and 62 (FIG. 17) of the retainer 14 may be received in the notches 80 and 82, respectively, at the ends of the first and second upper slots 76 and 78, respectively, of the first end portion 40 such that the retainer 14 may be fixed with respect to the first end portion 40. The curved portion 56 of the retainer 16 may be positioned adjacent the cam surface 70 (FIG. 7) on the end cap 64 of the first end portion 40, and may be positioned around the tooth 72 such that the retainer 16 may slide with respect to the end cap 64 of the first end portion 40. The arms 52 and 54 of the retainers 14 and 16 may also be received in the first and second upper slots 76 and 78 in an inner portion 66 of the second end portion 42. The ends 60 and 62 of the retainer 16 may be received in the notches 80 and 82, respectively, at the ends of the first and second upper slots 76 and 78, respectively, of the second end portion 42 such that the retainer 16 may be fixed with respect to the second end portion 42. The curved portion 56 of the retainer 14 may be positioned adjacent the cam surface 70 on the end cap 64 of the second end portion 42, and may be positioned around the tooth 72 such that the retainer 14 may slide with respect to the end cap 64 of the second end portion 42.

Similarly, at least a portion of the retainers 18 and 20 may be positioned beside each other and generally inside the body portion 12 when in the deployed or undeployed position. As shown in FIG. 16, the arms 52 and 54 of the retainers 18 and 20 may be received in the first and second lower slots 84 and 86 in the inner portion 66 of the first end portion 40. The ends 60 and 62 (FIG. 17) of the retainer 18 may be received in the notches 90 and 88, respectively, at the ends of the first and second lower slots 86 and 84, respectively, of the first end portion 40 such that the retainer 18 may be fixed with respect to the first end portion 40. The curved portion 56 of the retainer 20 may be positioned adjacent the cam surface 70 (FIG. 7) on the end cap 64 of the first end portion 40, and may be positioned around the tooth 72 such that the retainer 20 may slide with respect to the end cap 64 of the first end portion 40. The arms 52 and 54 of the retainers 18 and 20 may also be received in the first and second lower slots 84 and 86 in an inner portion 66 of the second end portion 42. The ends 60 and 62 of the retainer 16 may be received in the notches 90 and 88, respectively, at the ends of the first and second lower slots 86 and 84, respectively, of the second end portion 42 such that the retainer 20 may be fixed with respect to the second end portion 42. The curved portion 56 of the retainer 18 may be positioned adjacent the cam surface 70 on the end cap 64 of the second end portion 42, and may be positioned around the tooth 72 such that the retainer 18 may slide with respect to the end cap 64 of the second end portion 42.

Figure 9:
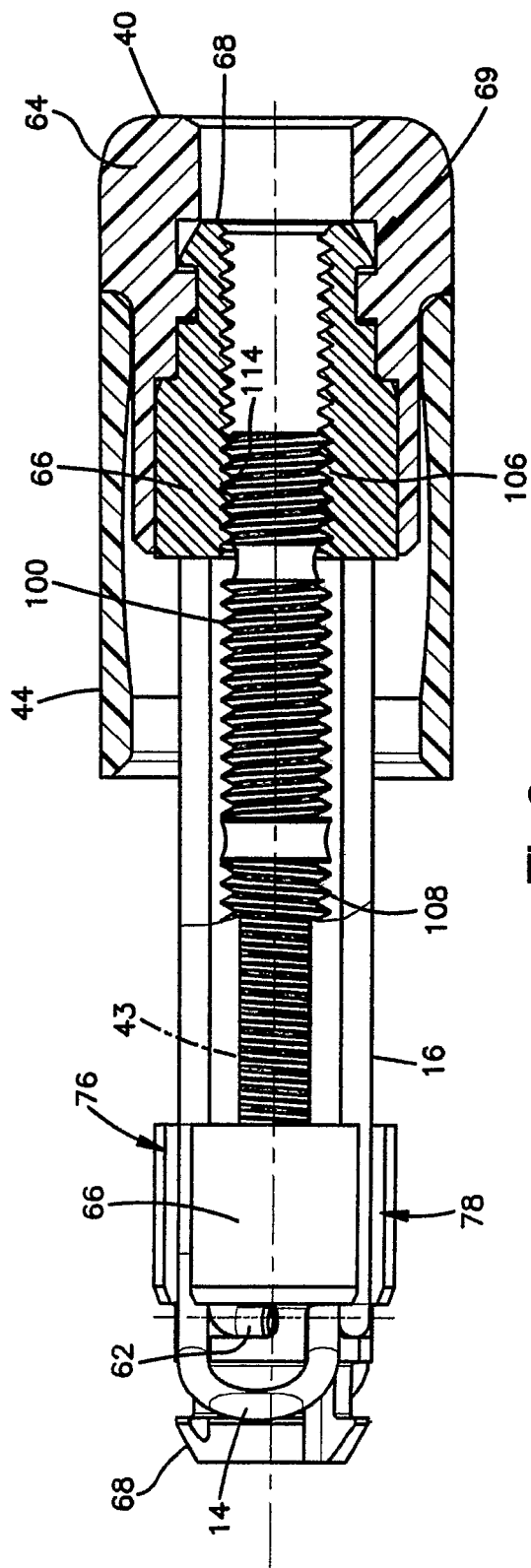
FIG. 9 is a side view showing a partial cross-section of the implant of FIG. 2 with certain portions of the implant not illustrated.

As shown in FIGS. 7-9, the end cap 64 and inner portion 66 of the second end portion 42 may be identical to the end cap 64 and inner portion 66 of the first end portion 40. Within the body portion 12, the retainers 14 and 16 generally may be positioned beside each other. The arms 52 and 54 of the retainers 14 and 16 may be received in the first and second upper slots 76 and 78 in the inner portion 66. The ends 60 and 62 (FIG. 17) of the retainer 16 may be received in the notches 80 and 82, respectively, at the ends of the first and second upper slots 76 and 78, respectively. The curved portion 56 of the retainer 14 may be positioned adjacent the cam surface 70 (FIG. 8) on the end cap 64, and may be positioned around the tooth 72. Similarly, the retainers 18 and 20 generally may be positioned beside each other in the body portion 12. The arms 52 and 54 of the retainers 18 and 20 may be received in the first and second lower slots 84 and 86 in the inner portion 66.

The ends 60 and 62 of the retainer 20 may be received in the notches 90 and 88, respectively, at the ends of the first and second lower slots 86 and 84, respectively. The curved portion 56 of the retainer 18 may be positioned adjacent the cam surface 70 on the end cap 64, and may be positioned around the tooth 72.

A connector 100 may extend along the axis 43 between the end portions 40 and 42 of the body portion 12. As shown in FIG. 18, the connector 100 may have external screw-threads and may have sections 102, 104. Each section 102 and 104 may have a recess 105 for receiving an actuation tool (e.g., actuation tool 184 of FIG. 36). The recess 105 may have gripping surfaces for engaging corresponding gripping surfaces on an actuation tool (e.g., the recess 105 may be polygonal in shape). The sections 102 and 104 also have respective screw threads 106 and 108 which may extend around the connector 100 in opposite directions relative to each other (e.g., section 102 may have right handed threads 106; section 104 may have left handed threads 108). As shown in FIGS. 7 and 9, the screw threads 106 and 108 on the connector 100 may engage corresponding internal screw threads 114 on the inner portions 66 of end portions 40 and 42 of the body portion 12. Such a configuration may enable the end portions 40 and 42 to move along the connector 100 axially toward or away from each other upon rotation of the connector 100 relative to the inner portions 66.

When the two end portions 40 and 42 move axially toward each other, the retainers 14, 16, 18 and 20 may move with respect to the end portions 40, 42. The retainers 14, 16, 18 and 20 may move with the end caps 64 and inner portions 66 to which the ends 60, 62 of the retainers 14, 16, 18 and 20 may be attached. As the end portion 40 moves, the retainers 14 and 18 which may be fixed in the end cap 64 of the first end portion 40 may also move so that the curved portions 56 of the retainers 14 and 18 may be pushed forcefully against the cam surfaces 70 on the end cap 64 of the second end portion 42. Similarly, as the end portion 42 moves, the retainers 16 and 20 which may be fixed in the end cap 64 of the second end portion 42 may also move so that the curved portions 56 of the retainers 16 and 20 may be pushed forcefully against the cam surfaces 70 on the end cap 64 of the first end portion 42. The cam surfaces 70 may guide the curved surfaces 56 so that the retainers 16 and 20 may move outward through the openings 73 in the end cap 64 of the first end portion 40 and the retainers 14 and 18 may move outward through the openings 73 in the end cap 64 of the second end portion 42. More specifically, the arms 52 and 54 of the retainer wires 50 may also move outward through the openings 73 as the end portions 40 and 42 of the body structure 12 continue to move axially toward each other. The arms 52 and 54 may be deflected (e.g., along an arcuate or straight path) as the arms 52 and 54 slide outward against the cam surfaces 70. The retainers 14, 16, 18 and 20 may be pre-bent so that they resume the bent configuration once extended from the ends 40, 42 (e.g., the retainers 14, 16, 18 and 20 may have a shape memory). Alternatively, the retainers 14, 16, 18 and 20 may be deformed (elastically or plastically) as the retainers 14, 16, 18 and 20 move out of the body portion 12. When the retainers 14, 16, 18 and 20 extend out of the end portions 40, 42, the retainers 14, 16, 18 and 20 may be positioned around adjacent spinous processes in the deployed position, and the retainers 14, 16, 18 and 20 may help to hold the device in position or retain the device between adjacent spinous processes as shown in FIG. 1. In a deployed position, the retainers 14, 16, 18 and 20 may extend away from the body a length L1 (FIG. 1) which may be, for example, between about 0.2 inches and 2.0 inches, more preferably, between about 0.3 inches and 1.0 inch and, most preferably, between about 0.4 inches and about 0.6. inches. Moreover, in a deployed position, the retainers 14 and 16, 18 and 20 may have a dimension D2 (FIG. 1) between adjacent retainers 14 and 16, 18 and 20 which may be substantially the same as the length L2 of the sleeve 44 (FIG. 19). The dimension D2 may be at least, for example, between about 0.1 inch and 2.0 inches, more preferably, between about 0.2 inches and 1.0 inches and, most preferably, between about 0.4 inches and about 0.5 inches. Moreover, In addition, retainers 14, 16, 18 and 20 may be retracted into the body portion 12.

The sleeve 44 may also help to hold the body portion 12 in position between adjacent spinous processes as shown in FIG. 1. In the expanded configuration of FIG. 2, the sleeve 44 may be freely movable axially and rotationally relative to the other parts of the implant 10 (e.g., the end portions 40, 42 and retainers 14, 16, 18 and 20). In the contracted configuration of FIG. 3, the sleeve 44 may be captured between the end portions 40 and 42 and may be prevented from moving axially about axis 43. In one embodiment, the sleeve 44 may be fixed with respect to the connector 100 such that the sleeve 44 may not move axially relative to the connector 100. The sleeve 44 may, however, be free to rotate relative to the end portions 40 and 42 as well as the retainers 14, 16, 18 and 20. If bending or other movement of the spine causes the spinous processes 24 and 26 to impart rotational forces to the sleeve 44, those forces may be dissipated by rotation of the sleeve 44 relative to the other parts of the implant 10. Such a construction may prevent the transmission of rotational forces from the sleeve 44 to the retainers 14, 16, 18 and 20 and, thereby, may help prevent unwanted rotation and/or displacement of the retainers 14, 16, 18 and 20.

As shown in FIG. 19, the sleeve 44 may have an outer surface 120 with a diameter D, which may be uniform along the length of the sleeve 44 (e.g., the sleeve may have a cylindrical contour). For example, the diameter may be between about 0.1 inches and about 1.0 inches, more preferably, between about 0.15 inches and about 0.8 inches and, most preferably, between about 0.235 inches and about 0.63 inches. The sleeve may have a thickness T, for example, between about 0.01 inches and about 0.15 inches, more preferably, between about 0.02 inches and about 0.07 inches and, most preferably, between about 0.035 inches and about 0.05 inches. As shown in FIG. 8, the end caps 64 of the end portions 40, 42 may have diameters which may be substantially similar to the diameter D. An inner surface 122 of the sleeve 44 may have a contour (e.g., convex contour) which may be curved radially outward. The inner surface 122 may define a tapered central section 124 of the sleeve 44 which may be thinner than the sections 126 at opposite ends of the sleeve 44. Such a construction may provide greater flexibility to the sleeve 44 at the central section 126 so that the sleeve 44 may be deflected radially inward under forces applied from the spinous processes 24 and 26.

Figure 7A:
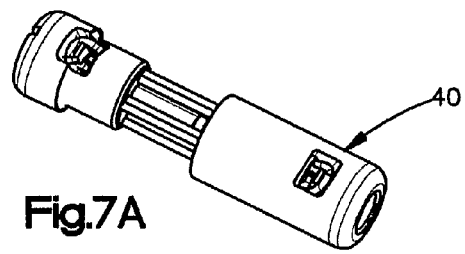
FIG. 7A is a perspective view of an exemplary embodiment of an alternative implant of the present invention.
Figure 7B:
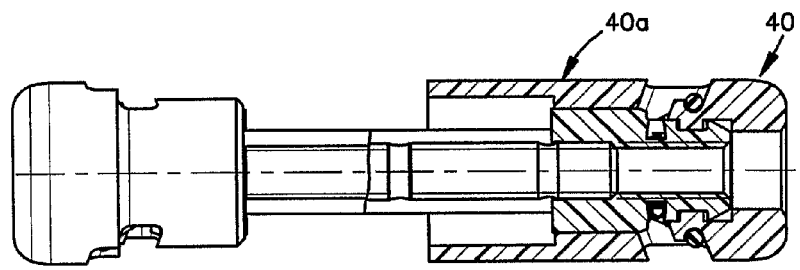
FIG. 7B is a side view showing a partial cross-section of the implant of FIG. 7A.
Figure 7C:
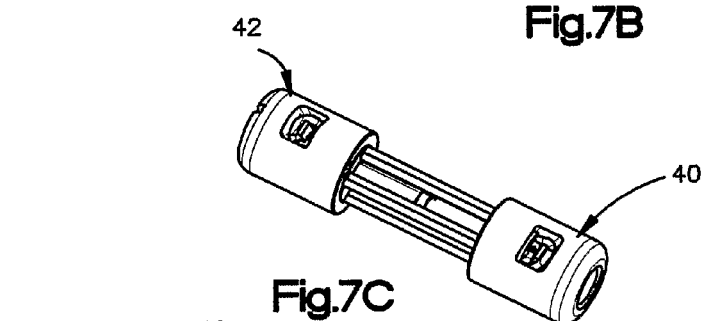
FIG. 7C is a perspective view of an exemplary embodiment of another alternative implant of the present invention.
Figure 7D:
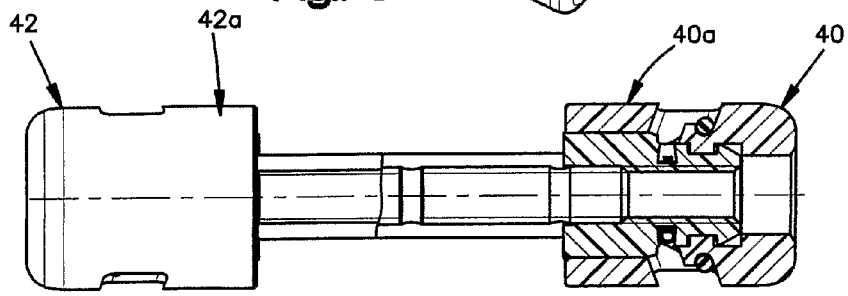
FIG. 7D is a side view showing a partial cross-section of the implant of FIG. 7C.

It should be noted that in some embodiments, a sleeve 44 may be unnecessary. For example, as shown in FIGS. 7A and 7B, the first end portion 40 may have an extended wall portion 40a. When the implant is in the contracted configuration, the extended wall 40a may be positioned between adjacent spinous processes. In an alternative embodiment, as shown in FIGS. 7C and 7D, the first end portion 40 and second end portion 42 may have extended wall portions 40a and 42a, respectively. When the implant is in the contracted configuration, the extended walls portions 40a, 42a may be positioned between the adjacent spinous processes.

In use, the body portion 12 may be inserted in the space 23 between the spinous processes 24 and 26 of adjacent vertebrae 28 and 30 (shown schematically). The body portion 12 may have a first, expanded configuration such as shown in FIG. 2. In such a configuration, the body may have a length L (FIG. 7) of, for example, between about 0.15 inches and about 5.0 inches, more preferably, between about 0.5 inches and about 2.0 inches and, most preferably, between about 1.2 inches and about 1.4 inches. In the first configuration, end portions 40 and 42 of the body structure 12 may be spaced apart from each other along a longitudinal central axis 43. The sleeve 44 may be positioned between the end portions 40 and 42. In the expanded configuration, the retainers 14, 16 and 18, 20 may be located in a retracted or undeployed position such that the retainers 14, 16 and 18, 20 generally may be positioned within the body portion 12. Such a construction may enable the body portion to be inserted in between the spinous processes 24 and 26 from the side of the spine, (e.g., lateral insertion). Once the spinous spacer 10 is positioned between the spinous processes 24, 26, the body portion 12 may be moved to a second, contracted configuration such as shown in FIG. 3. To accomplish this, the end portions 40 and 42 may be moved axially toward each other. In the contracted configuration, the body 12 may have a length L (FIG. 7) of, for example, between about 0.05 inches and about 2.0 inches, more preferably, between about 0.5 inches and about 1.5 inches and, most preferably, between about 0.7 inches and about 0.9 inches. As the end portions 40 and 42 move towards each other, the retainers 14, 16, 18 and 20 may be moved out of the body 12 from the retracted position to the deployed position of FIG. 3. In the deployed position, the retainers 14 and 16 may extend away from the body portion 12 and may be positioned on opposite sides of the spinous process 24 on the vertebrae 28. The retainers 18 and 20 may extend away from the body portion 12 and may be positioned on opposite sides of the spinous process 26 on the vertebrae 30. In this arrangement, the body portion 12 may help maintain a desired spacing between the adjacent spinous processes 24 and 26. Furthermore, the retainers 14, 16, 18 and 20 may help to hold the body portion 12 in place with respect to the spine and/or surrounding soft tissue.

Various instruments may be used for insertion and/or removal of the implants 10 such as, for example, an implant holder 140, guide wire 170, dilator 176, insertion tubes 180, 182, actuation tool 184 and removal tool 290. While the instruments described below may be used with the implant 10, one of ordinary skill in the art will readily appreciate that any number of instruments may be used in place of those described herein.

Figure 22:
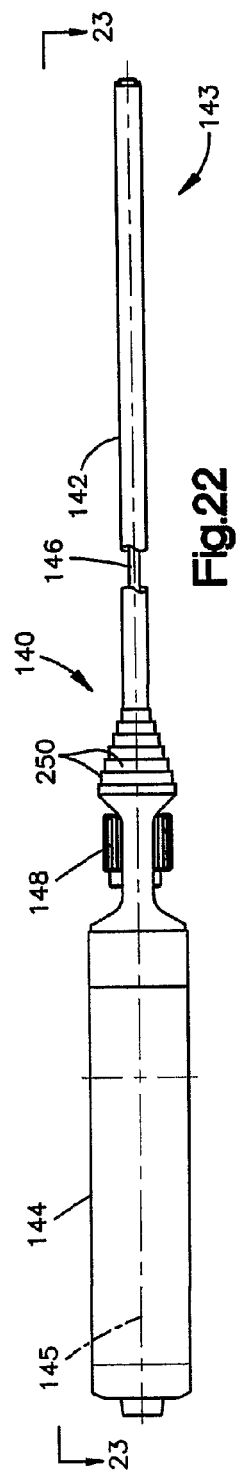
FIG. 22 is a side view of an exemplary embodiment of an implant holder of the present invention.
Figure 23:
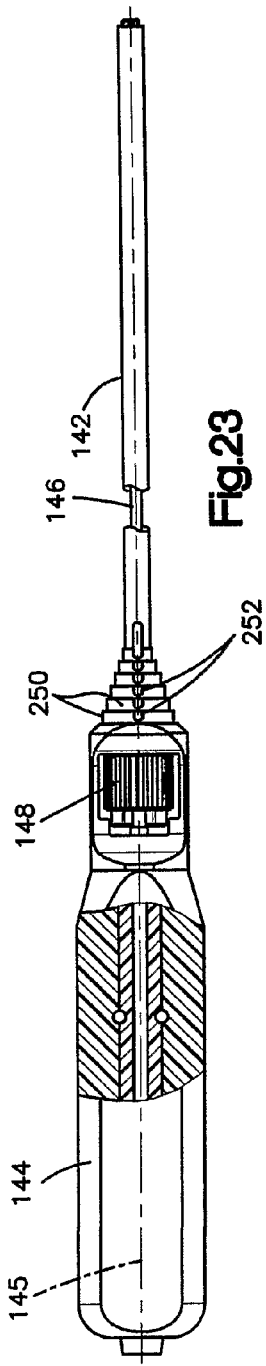
FIG. 23 is a partial cross-sectional view of the implant holder of FIG. 22 along line 23-23.
Figure 24:
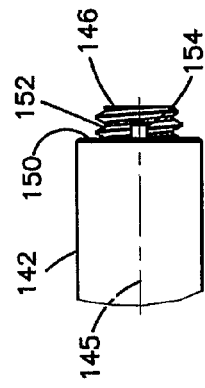
FIG. 24 is a side view of an exemplary distal portion of the implant holder of FIG. 22.

The implant holder 140 of FIGS. 22-24 may include an elongated stem 142 and a handle 144. The elongated stem 142 may be hollow (e.g., tubular) and may extend from the handle 144 and has a distal end 143. A wheel 148 may be positioned on the handle 144. A shaft 146, which may also be hollow, may extend through the stem 142, and may be operably connected to the wheel 148 so that rotation of the wheel 148 may result in rotation of the shaft 146 relative to the stem 142. As shown in FIG. 24, the distal end 143 of the shaft 146 may protrude from an open end 150 of the stem 142 and may have a screw-thread 152. A pair of protrusions 154, which may be diametrically opposed to each other (one of which is shown in FIG. 24), may project axially outward from the open end 150 of the stem 142 proximate the shaft 146. It should be noted that in some embodiments, one or more protrusions 154 may be used.

The implant inserter 140 may engage the first or second end portions 40, 42 and may be used as an insertion tool for moving the implant 10 into its installed position from the side of the spine. As shown in FIGS. 20 and 21, the end caps 64 of the first and/or second end portions 40, 42 may have a pair of slots 130 at an outer end 132. It should be noted, however, that the end portions 40, 42 may have one or more slots 130, which may be engaged by one or more protrusions 154 of the stem 142. Moreover, the first and/or second end portions 40, 42 may have an internal screw thread 134 which may extends axially inward from the outer end 132. The screw-thread 152 of the shaft 146 may engage the screw thread 134 of the first or second end portions 40, 42. Thereafter, the wheel 148 may be rotated to draw the holder 140 and, consequently, the protrusion(s) 154 of the holder 140 towards the first or second end portions 40, 42 so that the protrusion(s) 154 may be inserted into the slot(s) 130 of the first or second end portions 40, 42. The construction of the end portions 40, 42 and the holder 140 may prevent the end portions 40, 42 and retainers 14, 16 18 and 20 from rotating relative to the holder 140 about the axis 43.

The spinous spacer 10 may be inserted into the body using, for example, a lateral approach to the spine. An incision may be made in a patient's side. A guide wire 170, such as shown in FIG. 25, may be inserted through the incision. A distal end 194 of the guide wire 170 may be sharpened to assist the guide wire 170 in penetrating soft tissue. A proximal end 190 of the guide wire 170 may have an engagement portion such as, for example, an inner screw-threaded counterbore 192. A surgeon may grasp the guide wire 170 directly or may use a holder 172 to hold the guide wire 170. The holder 172 may have a handle 172, a passage 195, and a tightening member, such as a screw 196, intersecting the passage 195. The guide wire 170 may be clamped in place in the passage 195 by tightening the screw 196. The guide wire 170 may be attached to the holder 172 before or after the guide wire 170 is inserted into the body. In many cases, the guide wire 170 may be long enough for a surgeon to extend the distal end 194 of the guide wire 170 into the space 23 between the adjacent spinous processes 24 and 26. However, in some cases a surgeon may have to extend the length of the guide wire 170 using an extension 174.

The extension 174 may be an elongated member (e.g., rod or bar) having a distal end 200 and a proximal end 202. The distal end 204 may have a engagement portion 204, which may be in the form of screw threads. The distal end 204 may have a reduced diameter as compared to the rest of the extension 174. The engagement portion 204 of the extension 174 may be screwed into the counterbore 192 in the proximal portion 190 of the guide wire 170.

Figure 28:
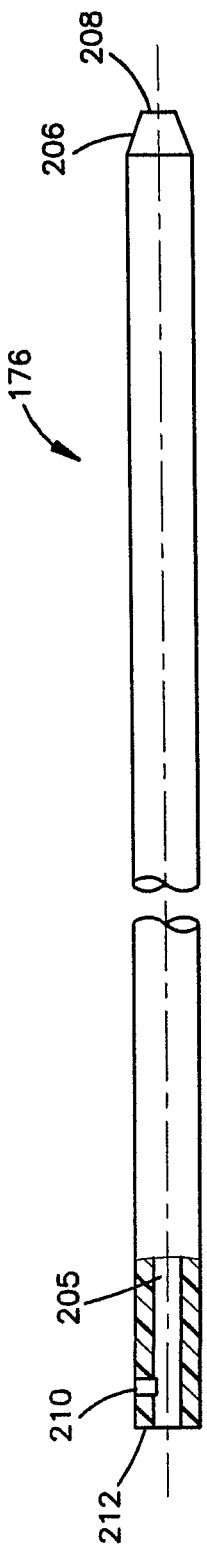
FIG. 28 is a partial cross-sectional side view of an exemplary embodiment of a dilator of the present invention.
Figure 29:
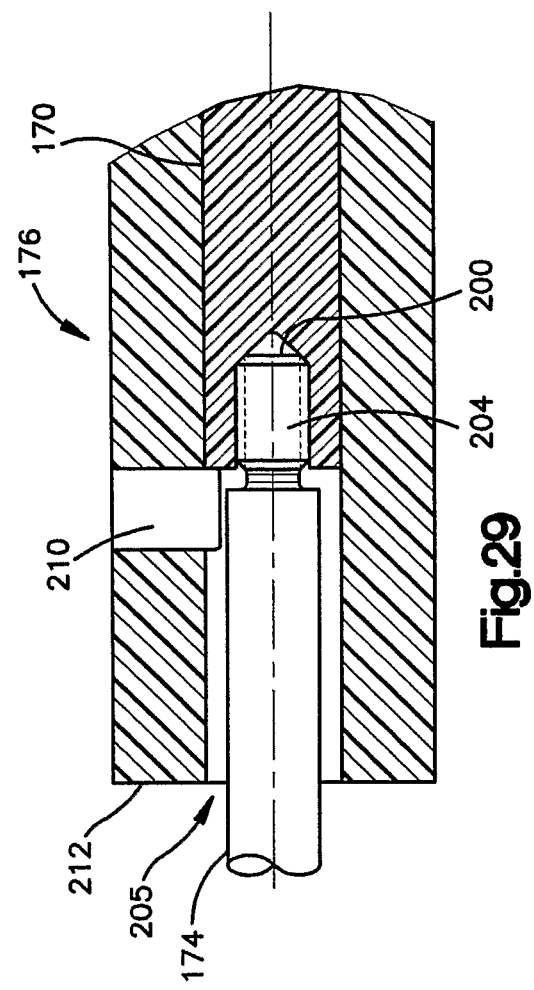
FIG. 29 is an enlarged, cross-sectional view of a proximal portion of an assembled guide wire of FIG. 25, guide wire extension of FIG. 27, and dilator of FIG. 28.

After the guide wire 170 is in place in the body, a dilator 176 may be positioned over the guide wire 170 and/or extension 174 (if used), and may be moved toward the spine by sliding the dilator 176 along the guide wire 170 and/or extension 174. As shown in FIG. 28, the dilator 176 may be a hollow tubular structure with a passage 205 therethrough. The distal end 208 of the dilator 176 may have a tapered surface 206. As the tapered surface 206 of the dilator 176 moves toward and into the space 23 between the spinous processes 22 and 24, the tapered end 206 may dilate the soft tissue. A pin 210 may extend into the passage 205 near the proximal end 212. As shown in FIG. 29, the dilator 176 may be positioned and moved over the guide wire 170 and/or extension 174 until the pin 210 engages the proximal end 190 of the guide wire 170 and/or proximal end 202 of the extension 174. The length of the dilator 176 may be correlated to the length of the guide wire 170 such that the pin 210 on the dilator 176 may abutment the proximal end 190 of the guide wire 170 to prevent movement of the dilator 176 once the tapered surface 206 reaches the space 23 between the spinous processes 24 and 26. It should be noted that one or more sequential dilators may be placed over the dilator 176 and may be used to dilate the opening through tissue from the skin to the vertebrae.

After the dilator 176 is positioned in the body, tubes 180 and 182 may be positioned over the dilator 176. The tubes 180, 182 may be part of a set of tubes which differ in size (e.g., diameter/dimension) to accommodate different patient anatomies. For example, the diameter/dimension of the tubes may be between about 0.1 inches and about 1.0 inches, more preferably, between about 0.15 inches and about 0.8 inches and, most preferably, between about 0.25 inches and about 0.65 inches. The tube may be used to distract tissue as well as the space in between the spinous processes of adjacent vertebrae. The tube 180 of FIGS. 30-32 may have a configuration similar to the tube 182 of FIGS. 33-35. Tube 180 may have a smaller diameter and may be shorter than tube 182. All tubes in the set of tubes, including tubes 180, 182 may be cylindrical and each tube with a larger diameter may be sized to fit closely over the tube with the next smallest diameter. In this way, all of the tubes in the set may be nested concentrically together. In addition, certain tubes may correspond to the different sized devices 10. These tubes may be configured such that the tube has an inner diameter closely matching the outer diameter D of the spinous spacer 10. Such a construction may enable a device 10 to slide closely and smoothly through its corresponding tube when the spinous spacer 10 is in the extended configuration of FIG. 2. The tubes may also have two slots 260 which may enable retainers 14, 16, 18 and 20 to be deployed through the tube as described below. In other embodiment the tubes may have one slot 260.

In use, the surgeon may first select a tube having a first dimension D1, such as, for example, the tube 180 shown in FIG. 30. Similar to other tubes, tube 180 may have a tapered distal end 220. The surgeon may move the tube 180 over the guide wire 170 and/or dilator 176 (i.e., the assembly of FIG. 29) so that the tube 180 may move along the dilator 176 toward the distal end 208 of the dilator 176. As the tapered distal portion 220 of the tube 180 is moved into the space 23 between the spinous processes 24 and 26, it may dilate the soft tissue as well as distract the spinous processes 24 and 26. Further dilation and distraction may be accomplished by moving successively larger dimensioned tubes over smaller tubes. This process may be repeated until dilation and distraction is completed by a final outermost tube such as, for example, tube 182 of FIG. 33 (i.e., dilation/distraction continues until adjacent spinous processes are separated by a desired distance). In order to help properly position the tubes in between adjacent vertebrae, the tubes may have at least one pair of indication slots 266. The indication slots 266 may be spaced axially from the distal end 262 of the tubes and may be diametrically opposed to each other. When looking at the tubes 180, 182 from the view shown in FIGS. 30 and 33, the indication slots 266 may overlap each other and may be oriented at an angle with respect to each other. For example, the indication slots 266 may be at a 90 degree angle to each other so that their overlapping x-ray image may form an "X" when the tube is viewed in the orientation shown in FIG. 30 or 33. Such a configuration may be used to produce shapes when viewing an x-rays. As shown in the embodiment of FIGS. 30 and 33, another pair of indication slots 268 may be provided on tube 180, 182 more proximal than slots 266. The pairs of indication slots 266 and 268 may enable a surgeon to rotate the tube until the "X" images are formed in an x-ray view from the rear of the spine. Once the "X" image is visible, this may indicate that the tube and, in particular, the slots 266 are correctly oriented for deployment of the retainers 14, 16, 18 and 20 therethrough.

As seen in FIG. 33, each tube may have a knob 222 at its proximal end 224 which may project inwardly in the passage through the tube. When a larger tube is placed over a smaller tube, the knob 222 on the larger tube may move into abutment with the distal most end 224 of the smaller tube. Such a construction may limit movement of larger tubes over small tubes so that the tapered distal end 220 of the concentric tubes overlap at the same location between the spinous processes 24 and 26.

Each tube may also have a pair of slots 230 at its proximal end 224. The slots 230 may delineate an opposed pair of sections 232, which may be deflectable. The section 232 may be axially aligned with the knob 222 but may be spaced a short distance axially from the knob 222. In order to remove smaller tubes (e.g., tube 180) from the outermost tube 182, a surgeon may push the proximal end 224 at a location 224*a* opposite the knob 222 (e.g., at a location approximately 180 degrees from the knob) in a direction towards the knob 222 (e.g., in a direction perpendicular to the longitudinal axis of the outermost tube 182). The slots 230 may enable the proximal end 224 of the tube 182, including the knob 222 and sections 232, to be deflected upward as shown in FIG. 30 so that the concentric inner tubes can be removed together from the outermost tube 182. The guide wire 174 and the dilator 176 may also be removed from the outermost tube 182. With the tube 182 positioned in between the spinous processes 24 and 26, the surgeon may select a device 10 of a size corresponding to the inner dimension of the outermost tube 182. A surgeon may then attach the selected device 10 to the implant holder 140, and may move the device 10 through the tube 182 towards and in between the spinous processes 24 and 26. The implant 10 is connected to the implant holder preferably so that the longitudinal axis of the implant 10 is aligned and coincident with the longitudinal axis of the implant holder 140.

The implant holder 140 may be inserted into the tube 182 until the proximal most portion 224 of the outermost tube engages a stepped portion 250 (FIGS. 22 and 23) of the holder 140. The stepped portion 250 may have dimensions so that each step matches the inner diameters of a tube in the set of tubes (e.g., tubes 180, 182). Each step 250 may also have a notch 252 to receive the knob 222 on the corresponding tube. Such a construction may assist in positioning the implant in the proper location between adjacent spinous processes 24, 26 (i.e., the stepped portion 250 may act as a stop, which may prevent the device 10 from being inserted too far through the tube) as well as aligning the retainers 14, 16, 18 and 20 with the slots 260 (i.e., positioning the knob 222 in the notch 252 may prevent rotational misalignment).

During insertion of dilator, dilation tubes and/or insertion tubes substantial resistance caused by soft tissues, scar tissues or ligaments may be encountered. At times, even the use of a hammer may be necessary to allow controlled insertion of these instruments. Resistance to insertion of instruments may make it more difficult to insert instruments in the body if the outer diameters of these instruments are too small to provide appropriate grip for the surgeon's hands. As shown in FIG. 35A, a handle 600 may be used to provide an enhanced gripping surface to insert, for example, dilator 176 and tubes 180 and 182. Additionally, the handle may provide a surface for hammering the instruments into the body without causing damage to the instruments. The handle 600 or its portions may be made of, for example, polymer, metal or ceramic.

The handle 600 may be configured so that the handle 600 may be adapted to instruments having different dimensions. For example, the handle 600 may be designed to engage instruments which have a dimension or diameter of between about 8 mm and about 18 mm. The handle 600 may have an ergonomically shaped body 601 and an engagement mechanism to grip the different dimensioned instruments. The engagement mechanism may be similar to parallel forceps. As illustrated in FIGS. 35B and 35C, the engagement mechanism may have a plurality of prongs 602 which may engage on the outer surface of an instrument (e.g. tube 180, 182) to grip the instrument. At least one prong 602 may have one or more ridges 604 for engaging an instrument. In an embodiment where the handle 600 is used with the tube 180, 182, the ridges 604 may engage one or more slots 270 of the tube 180, 182. Rotational movement about the axis of the tube 180, 182 and linear movement perpendicular to the axis of tube 180, 182 (i.e., away from the axis of the tube) may be prevented by the engagement of the ridges 604 with the slots 270.

The prongs 602 may be moved relative to each other (e.g., towards and/or away from each other) by movement of a knob 610. The knob 610 may have a cap 620 and a locking mechanism 630, which may be threaded. The cap 620 may be designed so that a surgeon may impact the cap 620 with a hammer. For instance, the cap 620 may be made of a material which may reduce peak loads at the impact of hammering (e.g., polymer, metal, ceramic). Movement of the cap 620 along the axis A of the handle 600 may move the prongs 602 relative to each other. As the cap 620 is pushed forward towards distal end 603, the prongs 602 may open, thereby allowing an instrument to be inserted into the body 601. The prongs 602 may be spring loaded so that the prongs 602 may close when the cap 620 is released, thereby engaging the instrument (e.g., tube 180, 182). In order to prevent the prongs 602 from inadvertently opening and/or separating from the instrument, the locking mechanism 630 may be rotated until the locking mechanism 630 engages the body 601 of the handle 600. It will be appreciated that other means of moving and locking the prongs 602 are envisioned. Moreover, while the handle 600 is described in the context of use with spinal instruments, those skilled in the art will appreciate that the handle 600 may sized and configured to engage other instruments for performing procedures anywhere else in or on the body.

Figure 36:
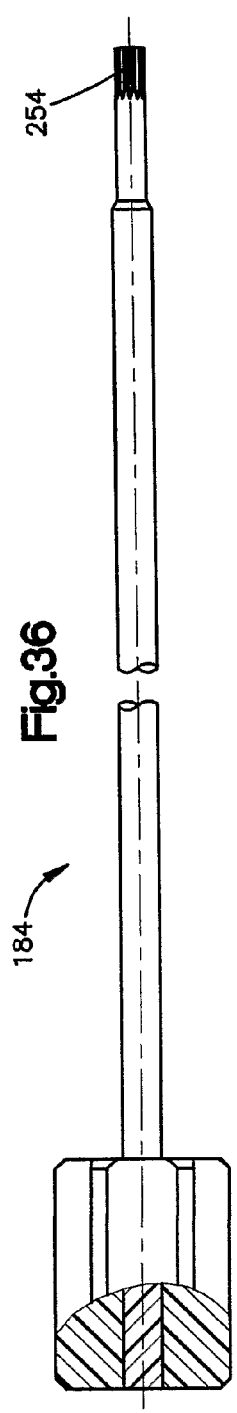
FIG. 36 is a partial side view of an exemplary embodiment of an implant actuation tool of the present invention.

Once the device 10 and holder 140 are in place (i.e., at the distal end 220 of the tube 182), the actuation tool 184 shown in FIG. 36 (e.g., screwdriver) may be inserted through the hollow shaft 146 on the holder 140. Alternatively, the holder 140, actuation tool 184 and device 10 may be attached together before placement in the body and inserted into the body as a single unit. The tool 184 may be inserted through the holder 140 until an engagement portion 254 of the tool 184 is received in the recess 105 of the connector 100. The tool 184 may then be rotated while the holder 140 is held in position. The tool 184 may cause the connector 100 to rotate and the holder 140 may prevent rotational movement of the end portions 40, 42. In this way, the end portions 40, 42 may move axially along the axis 43 towards each other. As the end portions 40, 42 move towards each other, the retainers 14, 16, 18 and 20 may be deployed from the body portion 12 and may be positioned around adjacent spinous processes 24, 26. It should be noted that the end portions 40, 42 may move towards each other until the retainers 14, 16, 18 and 20 tightly grip or firmly engage the spinous processes, thereby holding the device 10 in place. The distance between the end portions 40, 42 when the retainers 14, 16, 18 and 20 are in the fully deployed position may depend on the length L1 of the retainers 14, 16, 18 and 20 when at least a portion of the retainers 14, 16, 18 and 20 engage the spinous processes. The length L1 of the retainers 14, 16, 18 and 20, in turn, may depend on the width W (FIG. 1) of the spinous processes.

The retainers 14, 16, 18 and 20 may be deployed from the body portion 12 outwardly through the slots 260 of the tubes. The slots 260 may extend axially from the distal most end 262 of each tube towards the proximal end 224. The slots 260 may be diametrically opposed to each other and may be configured so that the tube 182 may be moved over the device 10 (e.g., slide on and off the device 10) after the retainers 14, 16, 18 and 20 have been deployed around the spinous processes. A pair of slots 270 near the proximal end 224 of the tubes may serve as viewing windows, which may enable an operator to align the slots 260 (and thereby the retainers 14, 16, 18 and 20) in the cranio-caudal direction.

With the retainers 14, 16, 18 and 20 deployed and the device 10 in position, the tool 184 may be withdrawn from the holder. The holder 140 may be detached from the device 10 by rotating the wheel 148. Thereafter, the holder 140 may be withdrawn from the tube 182. The tube 182 may then be removed from the patient, leaving the device 10 in between the adjacent spinous processes 24, 26.

Figure 37:
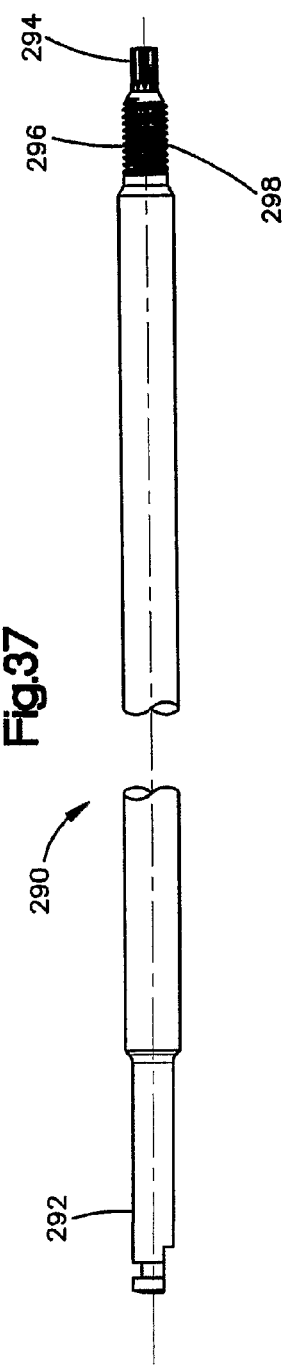
FIG. 37 is a side view of an exemplary embodiment of an implant removal tool of the present invention.

As shown in FIG. 37, a removal tool 290 may be used to retract retainers 14, 16, 18 and 20 into the body portion 12 and remove the device 10 from the body. The removal tool 280 may be a elongated member (e.g., rod) having a proximal end 292 and two distinct engagement portions 294 and 296. The proximal portion 292 may be sized and configured for engagement with a handle, drill or some other device which may impart rotation motion. The first engagement portion 296 may have a screw thread 298 so that the tool 290 may be inserted into the open outer end 132 (FIG. 21) of the end portion 64. The second engagement portion 294 may be sized and configured (e.g., may have a polygonal or hex shape) to engage the recess 105 (FIG. 18) of the connector 100.

In order to remove the spinous spacer 10 from the spine, a surgeon may use a lateral approach to the spine. An incision may be made in the side of a patient and the tool 290 may be inserted into the body until the second engagement portion 294 of the tool 290 may be inserted in the recess 105. The tool 290 may be used in place of the guide wire 170 and/or the extension 174. A dilator 176 may be inserted over the tool 290. Sequentially larger tubes 180, 182, etc. may be inserted over dilator 176 and into the space 23 between the adjacent spinous processes 24 and 26. When dilation and distraction are completed by placement of an outermost tube 182, the smaller tubes and/or dilator 176 may be removed from the tube 182.

The tool 290 and the connector 100 may then be rotated to drive the end portions 40 and 42 of the body portion 12 axially away from each other. As the body portion 12 moves from the contracted configuration of FIG. 3 to the expanded configuration of FIG. 2, the retainers 14, 16, 18 and 20 may be drawn back into the body portion 12 from the deployed positions to the retracted positions. As the end portion 42 moves axially toward the adjacent end of the connector 100, the screw thread 298 of the first engagement portion 296 may engage the internal screw thread 114 (FIGS. 7 and 9) of the inner portion 66 of the end portion 42. Such a configuration may cause the tool 290 to engage the device 10 in a manner similar to attachment of the implant holder 140. The rod 290 may then be used to pull the spinous spacer 10 through the tube 182.

Figure 40:
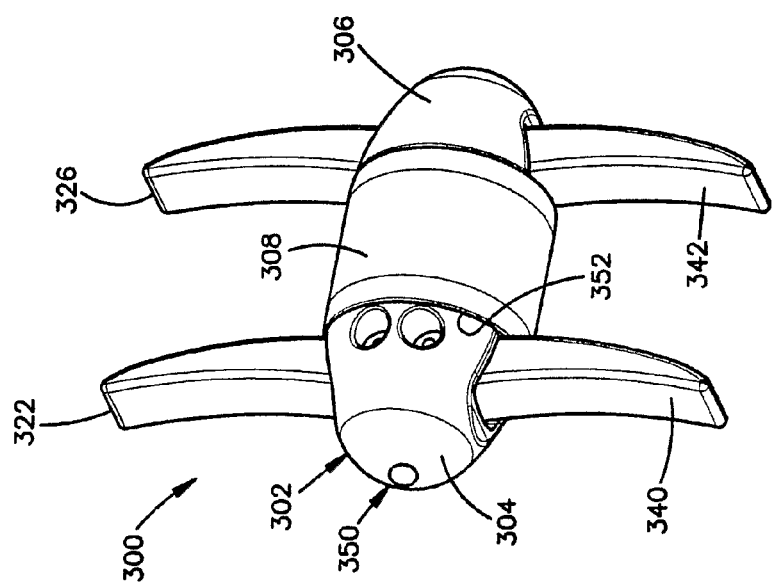
FIG. 40 is a perspective view of the implant of FIG. 38 in a second configuration.

FIGS. 38-40 illustrate another embodiment of an implant for treating spinal stenosis. The device 300 may be part of set of implants which may have different sizes to accommodate different anatomies. The body portions 302 may be configured for installation between a pair of adjacent spinal processes 24 and 26 (FIG. 1) by use of the installation devices described above. The body structure 302 may have first and second end portions 304 and 306, which may be centered on a longitudinal axis 307. A sleeve 308 may be freely movable axially and rotationally between the two end portions 304 and 306 of the body portion 302.

The first end portion 304 may have a base 310, which may be generally dome-shaped. A stem 312 may project axially from the base 310. The stem 312 may be any shape, for example, cylindrical. A first hinge 320 may operably connect a first retainer 322 to the base 310. Alternatively, the first hinge may operably connect the first retainer 322 to the stem 312. The hinge 320 may have a pivotal axis 323, which may be perpendicular to the longitudinal axis 307 of the body portion 302. First hinge 320 may comprise a pin about which the first retainer 322 may pivot or rotate. A second retainer 326 may be operably connected to the stem 312 by a second hinge 328, which may have a pivotal axis 329 which may be parallel to the first pivotal axis 323. Second hinge 328 may comprise a pin about which the second retainer 326 may pivot or rotate. A third and fourth retainer 340 and 342 may be operably connected to the base 310 and the stem 312, respectively, by a third and fourth hinge 344 and 346, respectively. The hinges 344 and 346 may have axes 347 and 349, respectively, which may be parallel to each other.

The device 300 may have an internal connector (not shown) which may be substantially similar to the connector 100 of the device 10. Accordingly, the connector of the implant 300 may have two sections with screw threads in opposite directions and each section may engage an end portion 304 and 306. Rotation of the connector about axis 307 may result in the end portions 304 moving axially toward each other. An opening 350 in the first end portion 302 may provide access for an actuation tool (e.g. screwdriver) to engage the connector such that the body portion 302 may be moved from the extended configuration of FIGS. 38 and 39 to the contracted configuration of FIG. 40.

When the end portions 304 and 306 are moved axially together, the first retainer 322 and the third retainer 340 may contact surface 352 of the sleeve 308, and the sleeve 308 as it moves will push the first and third retainers 322, 240 outwardly away from axis 307. Moreover, as the second end portion 306 moves inward, the second retainer 326 and the fourth retainer 342 may move or be pushed against cam surfaces 354, which may be positioned within openings 355 of the second end portion 306. In this way, the retainers 326 and 342 may move outwardly from the axis 307. The retainers 322, 326, 340 and 342 may thus be moved pivotally from retracted positions to deployed positions such that the retainers 322, 326, 340 and 342 may be positioned on opposite sides of the adjacent spinous processes 24 and 26. The sleeve 308 may be able to rotate and/or deflect under forces applied from the spinous processes 24 and 26 in the same manner as the sleeve 44 shown in FIG. 1.

Figure 41:
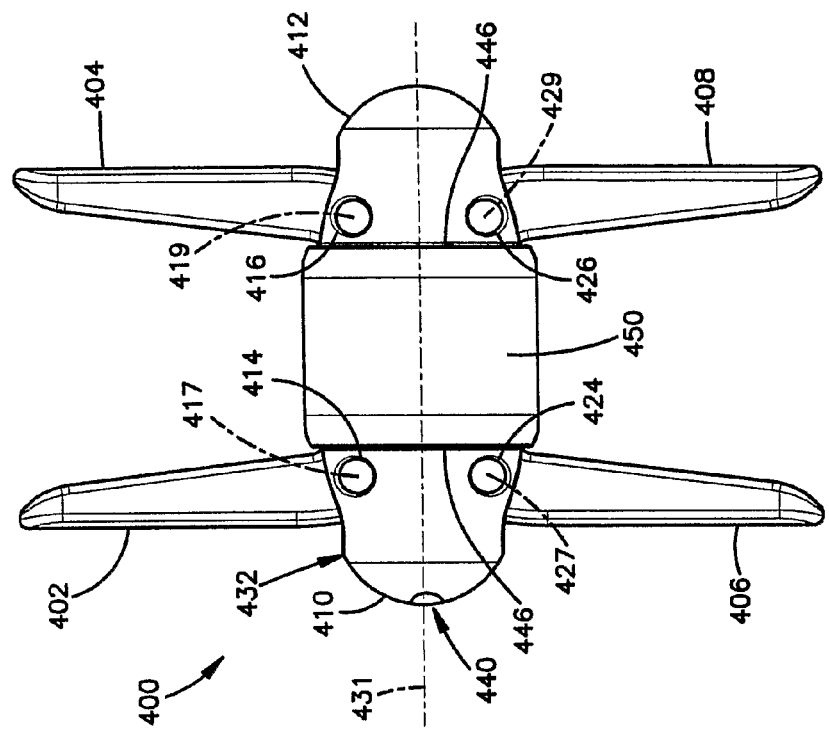
FIG. 41 is a side view of an exemplary embodiment of another alternative implant of the present invention.

FIG. 41 illustrates yet another embodiment of a device for treating spinal stenosis. The device 400 may have a body portion 432 and upper retainers 402, 404 and lower retainers 406, 408. The body portion 432 may have first and second end portions 410, 412 and a sleeve 450 positioned therebetween. The upper retainers 402 and 404 may be pivotally connected by hinges 414 and 416, respectively, on the first and second end portions 410 and 412. The hinges 414 and 416 may have pivotal axes 417 and 419, respectively, which may be parallel to each other. The lower retainers 406 and 408 may be pivotally connected by hinges 424 and 426, respectively, on first and second end portions 410 and 412. The hinges 424 and 426 may have pivotal axes 427 and 429 which are parallel to each other and parallel to the pivotal axes 417 and 419. All four pivotal axes 417, 419, 427 and 429 may be perpendicular to the longitudinal central axis 431 of the body portion 432.

A body portion 432 of a selected size may be installed between the adjacent spinous processes 24 and 26 (FIG. 1) using the installation devices described above. Once in position, an actuation tool (e.g., screwdriver) may be inserted through an access opening 440 in the first end portion 410 to actuate a connector (not shown) within the body portion 432. Similar to the connector 100, the connector of FIG. 41 may be rotated in order to draw the two end portions 410 and 412 axially together. In an expanded configuration, the retainers 402, 404, 406 and 408 may be positioned substantially parallel to the axis 431. As the two end portions 410, 412 are drawn together, the retainers 402, 404, 406 and 408 may be moved against surfaces 446 at the opposite ends of the sleeve 450. As shown in FIG. 41, this may cause the retainers 402, 404, 406 and 408 to pivot from retracted positions to deployed positions in which the retainers 402, 404, 406 and 408 may extend outward from the axis 431 and body portion 432. In the contracted configuration, the retainers 402, 404, 406 and 408 may deploy and hold the device 400 within the space 23 between the adjacent spinous processes 24 and 26. Moreover, the sleeve 450 may be able to rotate and/or deflect relative to the other parts of the device 400 (e.g., end portions 410, 412) under forces applied from the adjacent spinous processes 24 and 26.

Figure 42:
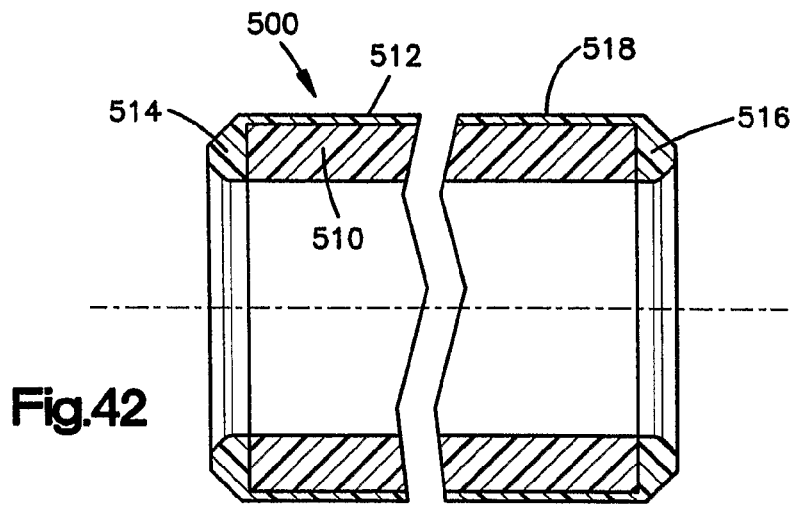
FIGS. 42-44 are cross-sectional views of alternative exemplary embodiments of the sleeves of the implants of FIGS. 2, 40 and 41.
Figure 43:
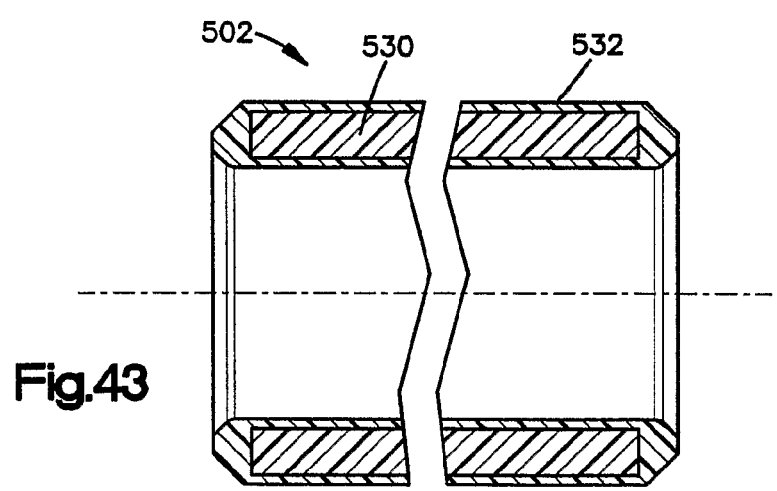
Figure 44:
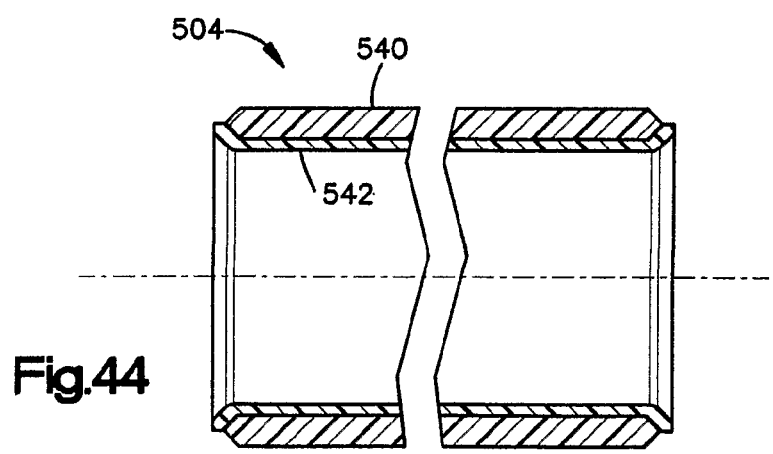

FIGS. 42, 43 and 44 illustrate alternative embodiments of sleeves 44, 308, and 450 described above. As shown in FIG. 42, sleeve 500 may have an inner and outer component 510 and 512. The outer component 512 may have end portions 514 and 516. A wall portion 518, which may be cylindrical, may extend axially between the end portions 514 and 516. The inner component 510 may be captured axially and rotationally within the outer component 512. The inner component may consist of a wall, which also may be cylindrical, with a thickness which may be substantially greater than the thickness of the surrounding wall portion 518 of the outer component 512.

The inner component 510 of the sleeve 500 may be formed of a material with different properties than the material used to form the outer component 512. For example, the inner component 510 may be formed of a material with a lower modulus of elasticity than the outer component 512. Using a more rigid material for the outer component 512, may result in the sleeve 500 being more resistant to wear under the influence of the adjacent spinous processes 24 and 26 (FIG. 1). Moreover, making the inner component 510 of a softer material may enable the sleeve 500 to be more flexible than if the sleeve 500 was formed entirely of a rigid material, similar to the material which may be used to make the outer component 512. The inner and outer components 510, 512 may be made of any suitable material, preferably biocompatible material, such as metal (e.g., stainless steel, titanium, aluminum, an alloy of two or more metals), plastic, rubber, ceramic, natural body tissue (e.g., bone) or a composite material (i.e., made up of two or more materials). In one embodiment, the outer component 512 of the sleeve may be made of polycarbonate, which may have a higher modulus of elasticity than polycarbonate urethane which may be used to make inner component 510.

As shown in FIG. 43, the sleeve 502 may have a component 530 formed of the softer, more flexible material which may be contained entirely within the surrounding structure of the component 532. The component 532 may be formed of the more rigid material than the material of component 530. Furthermore, in the sleeve 504 of FIG. 44, the outer component 540 may be made of a material which may have a lower modulus of elasticity than the material of the inner component 542. The softer outer material may results in less wear to adjacent spinous processes 24 and 26 positioned against the sleeve 504.

In one procedure, a lateral approach may be used to insert instrumentation into the body. In a lateral approach, instrumentation may be inserted through the side of a patient (e.g., the percutanous passageway may be oriented substantially perpendicular to the spinous processes or may be aligned with an axis passing between the spinous processes). A lateral approach may cause less trauma to soft tissues than the standard posterior approach used for insertion of interspinous spacers. This may due to the fact that the lateral approach may require only a small skin incision and blunt dissection of muscle and other soft tissues. Standard posterior approaches, on the other hand, may require a larger skin incision and detachment of muscles from the spinous processes. Muscle detachment may cause significant post operative pain and may impair proper functioning of the muscle. Blunt dissection of muscles may result in negligible post operative pain and preservation of muscle function. Therefore, a lateral approach may allow for shorter recovery times and patients can be dismissed from hospital within the same day of surgery. In other procedures, a posterior-lateral approach may be used for inserting instrumentation into the body.

To perform a lateral procedure, the patient may be positioned in a manner to cause the desired amount of reduction of the lordosis (i.e., the interspinous space to open up) at the desired level. This may be achieved with the patient in prone position with the chest oriented horizontally and the legs tilted towards the floor. The implant position in a lateral view can be predetermined by insertion of a guide wire through a small skin incision and into the interspinous space. This step may be performed with the help of x-ray control. The tip of the guide wire may indicate the future position of the implant. In some procedures, it may be necessary to use a longer guide wire. The guide wire may be extended by attaching an extension wire. The extension may enable a surgeon to hold the guide wire in place while one or more dilator 176, tubes 180, 182 or other instruments are being introduced into the body.

The passageway for the insertion of an implant may be prepared by stepwise dilation of soft tissues. Dilation may be achieved by introducing a first dilator 176 over the guide wire followed by dilation tubes 176 of increasing dimension/diameter (e.g., increments of 2 mm) until the outer diameter of the dilation tube 176 touches or slightly distracts the spinous processes. The outer diameter of the last dilation tube may be the same as the diameter of the interspinous spacer/implant which will be used. One or more insertion tube, for example tube 180, 182, may be positioned over the last/largest dilation tube between the spinous processes without causing any further distraction of the spinous processes. The insertion tube may create the passageway for the implant to be inserted between the spinous processes. With the outermost insertion tube in place, the guide wire dilator(s) and/or other insertion tube(s) may be removed from the body by, for example, pulling on the extension wire. This may clear the inner diameter of the outermost insertion tube.

Thereafter, the interspinous spacer/implant may be inserted through the insertion tube using an implant holder. The implant holder has stops which may ensure correct insertion depth and orientation of the implant. Once the implant is positioned between the spinous processes, the implant may be deployed on both sides of the spinous processes using a driving mechanism such as a screw driver. With the implant fully deployed, the implant holder may be detached and removed from the body with the insertion tube and the screw driver. Finally, the incision may be sutured closed.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

The invention claimed is:

1. A device configured to hold a surgical instrument, the surgical instrument having an outer surface and defining at least one slot, the device comprising:
   a body having a proximal end, a distal end and a passageway positioned therethrough;
   an instrument engagement device positioned in the passageway, the engagement device having at least two prongs moveable relative to each other and configured to hold the surgical instrument therebetween; and
   a knob at the proximal end of the body and operably associated with the at least two prongs so that movement of the knob causes movement of the at least two prongs relative to each other,
   wherein at least one prong has an inner surface defining a curved semi-circular profile in a direction transverse to a longitudinal axis of the at least one prong, the inner surface configured to at least partially conformingly engage the outer surface of the surgical instrument, the inner surface including at least one ridge extending from the inner surface in a direction along the longitudinal axis of the at least one prong, the ridge configured to substantially and conformingly engage the at least one slot of the surgical instrument,
   wherein the knob further comprises a cap at the proximal end positioned and designed for impact to facilitate movement of the surgical instrument.

2. The device of claim 1, wherein the body has an ergonomic shape.

3. The device of claim according to claim 1, wherein the knob comprises a locking mechanism which is rotatable relative to the body so as to fix the position of the prongs relative to each other.

4. The device according to claim 3, wherein the prongs move away from each other when the knob is pushed towards the distal end of the body and wherein the prongs are spring loaded so that the prongs move towards each other when the knob is released.

5. The device according to claim 1, wherein the prongs are located in the passageway and extend out the distal end of the body.

6. A device configured to hold a surgical instrument comprising:

a surgical instrument having an outer surface and defining at least one slot;

a holder comprising:
  a body having a proximal end, a distal end and a passageway positioned therethrough;
  an instrument engagement device positioned in the passageway, the engagement device having at least two prongs moveable relative to each other and configured to hold the surgical instrument therebetween; and
  a knob at the proximal end of the body and operably associated with the at least two prongs so that movement of the knob causes movement of the at least two prongs relative to each other,
wherein at least one prong has an inner surface defining a curved semi-circular profile in a direction transverse to a longitudinal axis of the at least one prong, the inner surface configured to at least partially conformingly engage the outer surface of the surgical instrument, the inner surface including at least one ridge extending from the inner surface in a direction along the longitudinal axis of the at least one prong, the ridge configured to at least substantially and conformingly engage the at least one slot of the surgical instrument.

7. The device of claim 6, wherein the body has an ergonomic shape.

8. The device of claim according to claim 6, wherein the knob comprises a locking mechanism which is rotatable relative to the body so as to fix the position of the prongs relative to each other.

9. The device according to claim 6, wherein the knob further comprises a cap at its proximal end positioned and designed for impact by a hammer to facilitate movement of the surgical instrument.

10. The device according to claim 6, wherein the prongs are located in the passageway and extend out the distal end of the body.

11. The device according to claim 1, wherein the inner surface of the at least one prong has a cylindrical curved shape configured to conformingly engage a cylindrical outer surface of the surgical instrument.

12. The device according to claim 11, wherein the at least one ridge has an elongate shape configured to extend axially along an axis of the cylindrical outer surface and at least one slot of the surgical instrument when engaging the at least one slot.

13. The device according to claim 6, wherein the inner surface of the at least one prong has a cylindrical curved shape configured to conformingly engage a cylindrical outer surface of the surgical instrument.

14. The device according to claim 13, wherein the at least one ridge has an elongate shape configured to extend axially along an axis of the cylindrical outer surface and at least one slot of the surgical instrument when engaging the at least one slot.

* * * * *